US008153128B2

(12) United States Patent
Bowers et al.

(10) Patent No.: US 8,153,128 B2
(45) Date of Patent: Apr. 10, 2012

(54) ANTIBODIES SPECIFIC FOR THE COMPLEX OF INTERLEUKIN-6 AND THE INTERLEUKIN-6 RECEPTOR

(75) Inventors: Keith Bowers, London (GB); Steven Godfrey Lane, London (GB); Philip Mallinder, London (GB); Isabelle Veronique Yolande Ossona De Mendez, London (GB)

(73) Assignee: MedImmune Limited, Cambridge (GB)

( * ) Notice: Subject to any disclaimer, the term of this patent is extended or adjusted under 35 U.S.C. 154(b) by 188 days.

(21) Appl. No.: 12/516,935

(22) PCT Filed: Nov. 28, 2007

(86) PCT No.: PCT/GB2007/004534
§ 371 (c)(1),
(2), (4) Date: Nov. 25, 2009

(87) PCT Pub. No.: WO2008/065384
PCT Pub. Date: Jun. 5, 2008

(65) Prior Publication Data
US 2010/0098709 A1 Apr. 22, 2010

Related U.S. Application Data

(60) Provisional application No. 60/861,705, filed on Nov. 30, 2006.

(51) Int. Cl.
*A61K 39/395* (2006.01)
*C07K 16/24* (2006.01)
(52) U.S. Cl. ............... 424/141.1; 530/387.1; 530/388.1
(58) Field of Classification Search ..................... None
See application file for complete search history.

(56) References Cited

U.S. PATENT DOCUMENTS

| | | | |
|---|---|---|---|
| 5,670,373 A * | 9/1997 | Kishimoto | 435/334 |
| 5,856,135 A | 1/1999 | Tsuchiya et al. | |
| 7,582,298 B2 * | 9/2009 | Stevens et al. | 424/143.1 |

FOREIGN PATENT DOCUMENTS

| | | |
|---|---|---|
| JP | 10-66582 | 10/1998 |
| WO | WO 2004/020633 A1 | 11/2004 |

OTHER PUBLICATIONS

Bataille, Régis et al., 1995, "Biologic Effects of Anti-Interleukin-6 Murine Monoclonal Antibody in Advanced Multiple Myeloma", Blood, 86(2):685-691.
Bell, S. J. et al., 2000, "Review article: the clinical role of anti-TNFα antibody treatment in Crohn's Disease", Aliment Pharmacol. Ther., 14:501-514.
Blay, Jean-Yves et al., 1997, "Role of Interleukin-6 in the Paraneoplastic Inflammatory Syndrome Associated With Renal-Cell Carcinoma" Int. J. Cancer, 72:424-430.
Boulanger, Martin J. et al., 2003, "Hexameric Structure and Assembly of the Interleukin-6/IL-6 α-Receptor/gp130 Complex", Science, 300:2101-2104.
Brakenhoff, Just P. J. et al., 1990, "Structure-Function Analysis of Human IL-6 Epitope Mapping of Neutralizing Monoclonal Antibodies with Amino-and Carboxyl-Treatment Deletion Mutants", The Journal of Immunology, 145(2):561-568.
Brakenhoff, Just P. J. et al., 1994, "Development of a Human Interleukin-6 Receptor Antagonist", The Journal of Biological Chemistry, 269(1):86-93.
Brochier, J. et al., 1995, "Immunomodulating IL-6 Activity by Murine Monoclonal Antibodies", Int. J. Immunopharm, 17(1):41-48.
Emilie, Dominique et al., 1994, "Administration of an Anti-Interleukin-6 Monoclonal Antibody to Patients With Acquired Immunodeficiency Syndrome and Lymphoma: Effect on Lymphoma Growth and on B Clinical Symptoms", Blood, 84(8):2472-2479.
Hirata, Yuuichi et al., 1989, "Characterization of IL-6 Receptor Expression by Monoclonal and Polyclonal Antibodies", The Journal of Immunology, 143:2900-2906.
Kalai, Michael et al., 1996, "Participation of two Ser-Ser-Phe-Tyr repeats in interleukin-6 (IL-6)-binding sites of the human IL-6 receptor", Eur. J. Biochem., 238:714-723.
Kalai, Michael et al., 1997, "Analysis of the mechanism of action of anti-human interleukin-6 and anti-human interleukin-6 receptor-neutralising monoclonal antibodies", Eur. J. Biochem.,., 249:690-700.
Kalai, Michael et al., 1997, "Analysis of the Human Interleukin-6/Human Interleukin-6 Receptor Binding Interface at the Amino Acid Level: Proposed Mechanism of Interaction", Blood, 89(4):1319-1333.
Lu, Zhao Yang et al., 1995, "Measurement of Whole Body Interleukin-6 (IL-6) Production: Prediction of the Efficacy of Anti-IL-6 Treatments", Blood, 86(8):3123-3131.
Menziani, M.C. et al., 1997, "Theoretical Investigation of IL-6 Multiprotein Receptor Assembly", Proteins: Structure, Function and Genetics, 29:528-544.
Mihara, Masahiko et al., 2005, "The therapy of autoimmune diseases by anti-interleukin-6 receptor antibody", Expert Opinion on Biological Therapy, 5(5):683-690.
Somers, William et al., 1997, "1.9 Å crystal structure of interleukin 6: implications for a novel mdoe of receptor dimerization and signaling", The EMBO Journal, 16(5):989-997. Varghese, J.N. et al., 2002, "Structure of the extracellular domains of the human interleukin-6 receptor α-chain", PNAS, 99(25):15959-15964.
Wendling, Daniel et al., 1993, "Treatment of Severe Rheumatoid Arthritis by Anti-Interleukin 6 Monoclonal Antibody", The Journal of Rheumatology,20:259-262.
Wijdenes, John et al., 1991, "Human Recombinant Dimeric IL-6 Binds to Its Receptor As Detected by Anti-IL-6 Monoclonal Antibodies", Molecular Immunology, 28(11): 1183-1192.
Zaanen, van H.C.T. et al., 1996, "Endogenous Interleukin 6 Production in Multiple Myeloma Patients Treated with Chimeric Monoclonal Anti-IL-6 Antibodies Indicates the Existence of a Positive Feed-back Loop", J. Clin. Invest., 98(6):1441-1448.
Zaanen, van H.C.T. et al., 1998, "Chimaeric anti-interleukin 6 monoclonal antibodies in the treatment of advanced multiple myeloma: a phase I dose-escalating study", Bristish Journal of Haematology,102:783-790.

* cited by examiner

*Primary Examiner* — Prema Mertz
(74) *Attorney, Agent, or Firm* — MedImmune Limited

(57) ABSTRACT

Binding members, especially antibody molecules that bind the IL-6:IL-6Ra complex formed by IL-6 and IL-6Ra, and do not bind either IL-6 or IL-6Ra alone. The binding members may have greater specificity for inhibiting pathological effects of IL-6 rather than beneficial effects of IL-6, as compared with binding members that bind IL-6 or IL-6Ra outside the IL-6:IL-6Ra complex.

6 Claims, No Drawings

SEQUENCE LISTING

```
<160> NUMBER OF SEQ ID NOS: 59

<210> SEQ ID NO 1
<211> LENGTH: 357
<212> TYPE: DNA
<213> ORGANISM: Homo sapiens
<220> FEATURE:
<223> OTHER INFORMATION: Antibody 1

<400> SEQUENCE: 1
gaggtgcagc tgttggagtc tgggggaggc ttggtacagc ctgggggtc cctgagactc      60 tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc ggcagcaacg     300
gggtggtctg agcctattga ctattgggc caagggacaa tggtcaccgt ctcgagt        357

<210> SEQ ID NO 2
<211> LENGTH: 119
<212> TYPE: PRT
<213> ORGANISM: Homo sapiens
<220> FEATURE:
<223> OTHER INFORMATION: Antibody 1

<400> SEQUENCE: 2

Glu Val Gln Leu Leu Glu Ser Gly Gly Gly Leu Val Gln Pro Gly Gly
                 5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Ala Thr Gly Trp Ser Glu Pro Ile Asp Tyr Trp Gly Gln Gly
            100                 105                 110

Thr Met Val Thr Val Ser Ser
        115

<210> SEQ ID NO 3
<211> LENGTH: 5
<212> TYPE: PRT
<213> ORGANISM: Homo sapiens
<220> FEATURE:
<223> OTHER INFORMATION: Antibody 1
```

-continued

<400> SEQUENCE: 3

Ser Tyr Ala Met Ser
                5

<210> SEQ ID NO 4
<211> LENGTH: 17
<212> TYPE: PRT
<213> ORGANISM: Homo sapiens
<220> FEATURE:
<223> OTHER INFORMATION: Antibody 1

<400> SEQUENCE: 4

Ala Ile Ser Gly Ser Gly Gly Ser Thr Tyr Tyr Ala Asp Ser Val Lys
                5                   10                  15
Gly

<210> SEQ ID NO 5
<211> LENGTH: 10
<212> TYPE: PRT
<213> ORGANISM: Homo sapiens
<220> FEATURE:
<223> OTHER INFORMATION: Antibody 1

<400> SEQUENCE: 5

Ala Thr Gly Trp Ser Glu Pro Ile Asp Tyr
                5                   10

<210> SEQ ID NO 6
<211> LENGTH: 327
<212> TYPE: DNA
<213> ORGANISM: Homo sapiens
<220> FEATURE:
<223> OTHER INFORMATION: Antibody 1

<400> SEQUENCE: 6
tcctatgtgc tgactcagcc accctcggtg tcagtggccc cagggcagac ggccacaatt      60
acctgtggag gaaacaatat tggacttaaa agtgtccact ggtaccagca gaagccaggc     120
caggcccctc tgctagtcgt ccatgatgat agcgcccggc cctcagggat cccggagcga     180
ttctctggct ccaactctgg gaacacggcc accctgacca tcagcagggt cgaagccggg     240
gatgaggccg actattcctg tcaggtttgg gataattctg gtggtctttg ggtgttcggc     300
ggagggacca aggtcaccgt cctaggt                                         327

<210> SEQ ID NO 7
<211> LENGTH: 109
<212> TYPE: PRT
<213> ORGANISM: Homo sapiens
<220> FEATURE:
<223> OTHER INFORMATION: Antibody 1

<400> SEQUENCE: 7

Ser Tyr Val Leu Thr Gln Pro Pro Ser Val Ser Val Ala Pro Gly Gln
                5                   10                  15

Thr Ala Thr Ile Thr Cys Gly Gly Asn Asn Ile Gly Leu Lys Ser Val
            20                  25                  30

His Trp Tyr Gln Gln Lys Pro Gly Gln Ala Pro Leu Leu Val Val His
        35                  40                  45

Asp Asp Ser Ala Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

-continued

Asp Glu Ala Asp Tyr Ser Cys Gln Val Trp Asp Asn Ser Gly Gly Leu
              85                  90                  95

Trp Val Phe Gly Gly Gly Thr Lys Val Thr Val Leu Gly
            100                 105

<210> SEQ ID NO 8
<211> LENGTH: 11
<212> TYPE: PRT
<213> ORGANISM: Homo sapiens
<220> FEATURE:
<223> OTHER INFORMATION: Antibody 1

<400> SEQUENCE: 8

Gly Gly Asn Asn Ile Gly Leu Lys Ser Val His
                5                   10

<210> SEQ ID NO 9
<211> LENGTH: 7
<212> TYPE: PRT
<213> ORGANISM: Homo sapiens
<220> FEATURE:
<223> OTHER INFORMATION: Antibody 1

<400> SEQUENCE: 9

Asp Asp Ser Ala Arg Pro Ser
                5

<210> SEQ ID NO 10
<211> LENGTH: 11
<212> TYPE: PRT
<213> ORGANISM: Homo sapiens
<220> FEATURE:
<223> OTHER INFORMATION: Antibody 1

<400> SEQUENCE: 10

Gln Val Trp Asp Asn Ser Gly Gly Leu Trp Val
                5                   10

<210> SEQ ID NO 11
<211> LENGTH: 366
<212> TYPE: DNA
<213> ORGANISM: Homo sapiens
<220> FEATURE:
<223> OTHER INFORMATION: Antibody 2

<400> SEQUENCE: 11
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggccgtgt attactgtgc tagagctggt    300
agcagtggct ggtatcttga ctggttcgac ccctgggggcc aggggacaat ggtcaccgtc   360
tcgagt                                                              366

<210> SEQ ID NO 12
<211> LENGTH: 122
<212> TYPE: PRT
<213> ORGANISM: Homo sapiens
<220> FEATURE:
<223> OTHER INFORMATION: Antibody 2

<400> SEQUENCE: 12

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Ser Ser Gly Trp Tyr Leu Asp Trp Phe Asp Pro Trp
            100                 105                 110

Gly Gln Gly Thr Met Val Thr Val Ser Ser
        115                 120

<210> SEQ ID NO 13
<211> LENGTH: 5
<212> TYPE: PRT
<213> ORGANISM: Homo sapiens
<220> FEATURE:
<223> OTHER INFORMATION: Antibody 2

<400> SEQUENCE: 13

Ser Tyr Ala Met Ser
            5

<210> SEQ ID NO 14
<211> LENGTH: 17
<212> TYPE: PRT
<213> ORGANISM: Homo sapiens
<220> FEATURE:
<223> OTHER INFORMATION: Antibody 2

<400> SEQUENCE: 14

Ala Ile Ser Gly Ser Gly Gly Ser Thr Tyr Tyr Ala Asp Ser Val Lys
                5                   10                  15

Gly

<210> SEQ ID NO 15
<211> LENGTH: 13
<212> TYPE: PRT
<213> ORGANISM: Homo sapiens
<220> FEATURE:
<223> OTHER INFORMATION: Antibody 2

<400> SEQUENCE: 15

Ala Gly Ser Ser Gly Trp Tyr Leu Asp Trp Phe Asp Pro
                5                   10

<210> SEQ ID NO 16
<211> LENGTH: 342
<212> TYPE: DNA
<213> ORGANISM: Homo sapiens
<220> FEATURE:
<223> OTHER INFORMATION: Antibody 2

<400> SEQUENCE: 16
caggctgtgc tgactcagcc gtcctcagtg tctggggccc caggacagag ggtcaccatc      60
tcctgcgctg ggagcagctc caacatcggg gcaggttatg atgtacactg gtatcagcaa     120
gttcctggaa cagcccccaa actcctcatt tatggtgaca ccaatcggcc ctcagggggtc    180

```
cctgaccgat tctctggctc caagtttggc acctcagcct ccctgaccat cactgggctc    240
caagctgagg atgaggctga ttattactgc cagtcctatg acaacagcct gagtacgtca    300
gattgggtct tcggcggggg gaccaaggtc accgtcctag gt                      342
```

```
<210> SEQ ID NO 17
<211> LENGTH: 114
<212> TYPE: PRT
<213> ORGANISM: Homo sapiens
<220> FEATURE:
<223> OTHER INFORMATION: Antibody 2

<400> SEQUENCE: 17
```

Gln Ala Val Leu Thr Gln Pro Ser Ser Val Ser Gly Ala Pro Gly Gln
              5                   10                  15

Arg Val Thr Ile Ser Cys Ala Gly Ser Ser Asn Ile Gly Ala Gly
         20                  25                  30

Tyr Asp Val His Trp Tyr Gln Gln Val Pro Gly Thr Ala Pro Lys Leu
             35                  40                  45

Leu Ile Tyr Gly Asp Thr Asn Arg Pro Ser Gly Val Pro Asp Arg Phe
50                  55                  60

Ser Gly Ser Lys Phe Gly Thr Ser Ala Ser Leu Thr Ile Thr Gly Leu
65                  70                  75                  80

Gln Ala Glu Asp Glu Ala Asp Tyr Tyr Cys Gln Ser Tyr Asp Asn Ser
                85                  90                  95

Leu Ser Thr Ser Asp Trp Val Phe Gly Gly Gly Thr Lys Val Thr Val
                100                 105                 110

Leu Gly

```
<210> SEQ ID NO 18
<211> LENGTH: 14
<212> TYPE: PRT
<213> ORGANISM: Homo sapiens
<220> FEATURE:
<223> OTHER INFORMATION: Antibody 2

<400> SEQUENCE: 18
```

Ala Gly Ser Ser Ser Asn Ile Gly Ala Gly Tyr Asp Val His
             5                   10

```
<210> SEQ ID NO 19
<211> LENGTH: 7
<212> TYPE: PRT
<213> ORGANISM: Homo sapiens
<220> FEATURE:
<223> OTHER INFORMATION: Antibody 2

<400> SEQUENCE: 19
```

Gly Asp Thr Asn Arg Pro Ser
             5

```
<210> SEQ ID NO 20
<211> LENGTH: 13
<212> TYPE: PRT
<213> ORGANISM: Homo sapiens
<220> FEATURE:
<223> OTHER INFORMATION: Antibody 2

<400> SEQUENCE: 20
```

Gln Ser Tyr Asp Asn Ser Leu Ser Thr Ser Asp Trp Val
             5                   10

<210> SEQ ID NO 21
<211> LENGTH: 366
<212> TYPE: DNA
<213> ORGANISM: Homo sapiens
<220> FEATURE:
<223> OTHER INFORMATION: Antibody 3

<400> SEQUENCE: 21

```
gaggtgcagc tgttggagtc tgggggaggc ttggtacagc ctgggggtc cctgagactc    60
tcctgtgcag cctctggatt cacctttagc agctatgcca tgagctgggt ccgccaggct   120
ccagggaagg gctggagtg gtctcagct attagtggta gtggtggtag cacatactac     180
gcagactccg tgaagggccg gttcaccatc tccagagaca attccaagaa cacgctgtat   240
ctgcaaatga acagcctgag agccgaggac acggccgtgt attactgtgc gaaagatgcc   300
gactacgaat tttggagtgg ttatttagac ttctggggcc agggaaccct ggtcaccgtc   360
tcgagt                                                              366
```

<210> SEQ ID NO 22
<211> LENGTH: 122
<212> TYPE: PRT
<213> ORGANISM: Homo sapiens
<220> FEATURE:
<223> OTHER INFORMATION: Antibody 3

<400> SEQUENCE: 22

```
Glu Val Gln Leu Leu Glu Ser Gly Gly Gly Leu Val Gln Pro Gly Gly
                 5                  10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Asp Ala Asp Tyr Glu Phe Trp Ser Gly Tyr Leu Asp Phe Trp
            100                 105                 110
Gly Gln Gly Thr Leu Val Thr Val Ser Ser
        115                 120
```

<210> SEQ ID NO 23
<211> LENGTH: 5
<212> TYPE: PRT
<213> ORGANISM: Homo sapiens
<220> FEATURE:
<223> OTHER INFORMATION: Antibody 3

<400> SEQUENCE: 23

```
Ser Tyr Ala Met Ser
                 5
```

<210> SEQ ID NO 24
<211> LENGTH: 17
<212> TYPE: PRT
<213> ORGANISM: Homo sapiens
<220> FEATURE:
<223> OTHER INFORMATION: Antibody 3

<400> SEQUENCE: 24

Ala Ile Ser Gly Ser Gly Gly Ser Thr Tyr Tyr Ala Asp Ser Val Lys
                5                   10                  15

Gly

<210> SEQ ID NO 25
<211> LENGTH: 13
<212> TYPE: PRT
<213> ORGANISM: Homo sapiens
<220> FEATURE:
<223> OTHER INFORMATION: Antibody 3

<400> SEQUENCE: 25

Asp Ala Asp Tyr Glu Phe Trp Ser Gly Tyr Leu Asp Phe
                5                   10

<210> SEQ ID NO 26
<211> LENGTH: 336
<212> TYPE: DNA
<213> ORGANISM: Homo sapiens
<220> FEATURE:
<223> OTHER INFORMATION: Antibody 3

<400> SEQUENCE: 26
cagtctgtgt tgacgcagcc gccctcagtg tctggggccc cagggcagag ggtcaacatc     60
tcctgcactg ggagcagctc aacatcgggg caggttatg atgtacactg gtaccagcag    120
cttccaggaa cagcccccaa actcctcatc tatggtaaca acaatcggcc ctcagggtc     180 cctgaccgat tctctggctc caagtctggc acctcagcct ccctggccat cactgggctc    240
caggctgagg atgaggctga ttattactgc cagtcctatg acagcagcct gagtggttat    300
gtcttcggga ctgggaccaa ggtcaccgtc ctaggt                              336

<210> SEQ ID NO 27
<211> LENGTH: 112
<212> TYPE: PRT
<213> ORGANISM: Homo sapiens
<220> FEATURE:
<223> OTHER INFORMATION: Antibody 3

<400> SEQUENCE: 27

Gln Ser Val Leu Thr Gln Pro Pro Ser Val Ser Gly Ala Pro Gly Gln
                5                   10                  15

Arg Val Asn Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Tyr Asp Ser Ser
                85                  90                  95

Leu Ser Gly Tyr Val Phe Gly Thr Gly Thr Lys Val Thr Val Leu Gly
            100                 105                 110

<210> SEQ ID NO 28
<211> LENGTH: 14
<212> TYPE: PRT
<213> ORGANISM: Homo sapiens
<220> FEATURE:
<223> OTHER INFORMATION: Antibody 3

<400> SEQUENCE: 28

Thr Gly Ser Ser Ser Asn Ile Gly Ala Gly Tyr Asp Val His
              5                   10

<210> SEQ ID NO 29
<211> LENGTH: 7
<212> TYPE: PRT
<213> ORGANISM: Homo sapiens
<220> FEATURE:
<223> OTHER INFORMATION: Antibody 3

<400> SEQUENCE: 29

Gly Asn Asn Asn Arg Pro Ser
              5

<210> SEQ ID NO 30
<211> LENGTH: 11
<212> TYPE: PRT
<213> ORGANISM: Homo sapiens
<220> FEATURE:
<223> OTHER INFORMATION: Antibody 3

<400> SEQUENCE: 30

Gln Ser Tyr Asp Ser Ser Leu Ser Gly Tyr Val
              5                   10

<210> SEQ ID NO 31
<211> LENGTH: 357
<212> TYPE: DNA
<213> ORGANISM: Homo sapiens
<220> FEATURE:
<223> OTHER INFORMATION: Antibody 4

<400> SEQUENCE: 31
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg gtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtgt attactgtgc gagagatgac     300
gactacgagg gctactttga ttactggggc cagggacaa tggtcaccgt ctcgagt        357

<210> SEQ ID NO 32
<211> LENGTH: 119
<212> TYPE: PRT
<213> ORGANISM: Homo sapiens
<220> FEATURE:
<223> OTHER INFORMATION: Antibody 4

<400> SEQUENCE: 32

Glu Val Gln Leu Leu Glu Ser Gly Gly Gly Leu Val Gln Pro Gly Gly
              5                   10                  15

Ser Leu Arg Leu Ser Cys Ala Ala Ser Gly Phe Thr Phe Ser Ser Tyr
         20                  25                  30

Ala Met Ser Trp Val Arg Gln Ala Pro Gly Lys Gly Leu Glu Trp Val
     35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
             85                  90                  95

Ala Arg Asp Asp Asp Tyr Glu Gly Tyr Phe Asp Tyr Trp Gly Arg Gly
            100                 105                 110

Thr Met Val Thr Val Ser Ser
            115

<210> SEQ ID NO 33
<211> LENGTH: 5
<212> TYPE: PRT
<213> ORGANISM: Homo sapiens
<220> FEATURE:
<223> OTHER INFORMATION: Antibody 4

<400> SEQUENCE: 33

Ser Tyr Ala Met Ser
                5

<210> SEQ ID NO 34
<211> LENGTH: 17
<212> TYPE: PRT
<213> ORGANISM: Homo sapiens
<220> FEATURE:
<223> OTHER INFORMATION: Antibody 4

<400> SEQUENCE: 34

Ala Ile Ser Gly Ser Gly Gly Ser Thr Tyr Tyr Ala Asp Ser Val Lys
                5                   10                  15

Gly

<210> SEQ ID NO 35
<211> LENGTH: 10
<212> TYPE: PRT
<213> ORGANISM: Homo sapiens
<220> FEATURE:
<223> OTHER INFORMATION: Antibody 4

<400> SEQUENCE: 35

Asp Asp Asp Tyr Glu Gly Tyr Phe Asp Tyr
                5                   10

<210> SEQ ID NO 36
<211> LENGTH: 339
<212> TYPE: DNA
<213> ORGANISM: Homo sapiens
<220> FEATURE:
<223> OTHER INFORMATION: Antibody 4

<400> SEQUENCE: 36
caggctgtgc tgactcagcc gtcctcagtg tctggggccc cagggcagag ggtcagcatc      60
tcctgcactg ggagtagttc caacatcggg gcaggttatg aagtacactg gtaccagcac     120
cttccaggaa cagcccccaa actcctcatc tatggtaaca acaatcgacc ctcagggg tc     180 cctgaccgat tctctggctc caagtctggc acctcagcct ccctggccat cactgggctc     240
caggctgaag atgaggctga ttattactgc agtcctatg acaacaacct gcctggttca     300
agggtgttcg gcggagggac caaggtcacc gtcctaggt                           339

<210> SEQ ID NO 37
<211> LENGTH: 113
<212> TYPE: PRT
<213> ORGANISM: Homo sapiens
<220> FEATURE:
<223> OTHER INFORMATION: Antibody 4

<400> SEQUENCE: 37

Gln Ala Val Leu Thr Gln Pro Ser Ser Val Ser Gly Ala Pro Gly Gln

-continued

```
                 5                   10                  15
Arg Val Ser Ile Ser Cys Thr Gly Ser Ser Asn Ile Gly Ala Gly
         20                  25                  30
Tyr Glu Val His Trp Tyr Gln His Leu Pro Gly Thr Ala Pro Lys Leu
         35                  40                  45
Leu Ile Tyr Gly Asn Asn Asn Arg Pro Ser Gly Val Pro Asp Arg Phe
         50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Asn Asn
                 85                  90                  95
Leu Pro Gly Ser Arg Val Phe Gly Gly Gly Thr Lys Val Thr Val Leu
         100                 105                 110
Gly

<210> SEQ ID NO 38
<211> LENGTH: 14
<212> TYPE: PRT
<213> ORGANISM: Homo sapiens
<220> FEATURE:
<223> OTHER INFORMATION: Antibody 4

<400> SEQUENCE: 38

Thr Gly Ser Ser Ser Asn Ile Gly Ala Gly Tyr Glu Val His
                         5                  10

<210> SEQ ID NO 39
<211> LENGTH: 7
<212> TYPE: PRT
<213> ORGANISM: Homo sapiens
<220> FEATURE:
<223> OTHER INFORMATION: Antibody 4

<400> SEQUENCE: 39

Gly Asn Asn Asn Arg Pro Ser
                         5

<210> SEQ ID NO 40
<211> LENGTH: 12
<212> TYPE: PRT
<213> ORGANISM: Homo sapiens
<220> FEATURE:
<223> OTHER INFORMATION: Antibody 4

<400> SEQUENCE: 40

Gln Ser Tyr Asp Asn Asn Leu Pro Gly Ser Arg Val
                         5                  10

<210> SEQ ID NO 41
<211> LENGTH: 366
<212> TYPE: DNA
<213> ORGANISM: Homo sapiens
<220> FEATURE:
<223> OTHER INFORMATION: Antibody 5

<400> SEQUENCE: 41
gaggtgcagc tgttggagtc tgggggaggc ttggtacagc ctgggggggtc cctgagactc     60 tcctgtgcag cctctggatt caccttttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtgt attactgtgc gagatctggc    300
```

```
ggttcgggga gttacttaag ttggttcgac ccctggggga aggggaccac ggtcaccgtc    360
tcgagt                                                                366
```

<210> SEQ ID NO 42
<211> LENGTH: 122
<212> TYPE: PRT
<213> ORGANISM: Homo sapiens
<220> FEATURE:
<223> OTHER INFORMATION: Antibody 5

<400> SEQUENCE: 42

Glu Val Gln Leu Leu Glu Ser Gly Gly Gly Leu Val Gln Pro Gly Gly
                5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Gly Gly Ser Gly Ser Tyr Leu Ser Trp Phe Asp Pro Trp
            100                 105                 110

Gly Lys Gly Thr Thr Val Thr Val Ser Ser
        115                 120

<210> SEQ ID NO 43
<211> LENGTH: 5
<212> TYPE: PRT
<213> ORGANISM: Homo sapiens
<220> FEATURE:
<223> OTHER INFORMATION: Antibody 5

<400> SEQUENCE: 43

Ser Tyr Ala Met Ser
                5

<210> SEQ ID NO 44
<211> LENGTH: 17
<212> TYPE: PRT
<213> ORGANISM: Homo sapiens
<220> FEATURE:
<223> OTHER INFORMATION: Antibody 5

<400> SEQUENCE: 44

Ala Ile Ser Gly Ser Gly Gly Ser Thr Tyr Tyr Ala Asp Ser Val Lys
                5                   10                  15

Gly

<210> SEQ ID NO 45
<211> LENGTH: 13
<212> TYPE: PRT
<213> ORGANISM: Homo sapiens
<220> FEATURE:
<223> OTHER INFORMATION: Antibody 5

<400> SEQUENCE: 45

Ser Gly Gly Ser Gly Ser Tyr Leu Ser Trp Phe Asp Pro
                5                   10

-continued

<210> SEQ ID NO 46
<211> LENGTH: 336
<212> TYPE: DNA
<213> ORGANISM: Homo sapiens
<220> FEATURE:
<223> OTHER INFORMATION: Antibody 5

<400> SEQUENCE: 46

```
cagtctgtgc tgacgcagcc gccctcagtg tctggggccc cagggcagag ggtcaccatc    60
tcctgcactg ggagcagctc aacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttgg   300
gtattcggcg gagggaccaa ggtcaccgtc ctaggt                             336
```

<210> SEQ ID NO 47
<211> LENGTH: 112
<212> TYPE: PRT
<213> ORGANISM: Homo sapiens
<220> FEATURE:
<223> OTHER INFORMATION: Antibody 5

<400> SEQUENCE: 47

Gln Ser Val Leu Thr Gln Pro Pro Ser Val Ser Gly Ala Pro Gly Gln
                5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Ser Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu Ser Gly Trp Val Phe Gly Gly Gly Thr Lys Val Thr Val Leu Gly
            100                 105                 110

<210> SEQ ID NO 48
<211> LENGTH: 14
<212> TYPE: PRT
<213> ORGANISM: Homo sapiens
<220> FEATURE:
<223> OTHER INFORMATION: Antibody 5

<400> SEQUENCE: 48

Thr Gly Ser Ser Ser Asn Ile Gly Ala Gly Tyr Asp Val His
                5                   10

<210> SEQ ID NO 49
<211> LENGTH: 7
<212> TYPE: PRT
<213> ORGANISM: Homo sapiens
<220> FEATURE:
<223> OTHER INFORMATION: Antibody 5

<400> SEQUENCE: 49

Gly Asn Ser Asn Arg Pro Ser
                5

```
<210> SEQ ID NO 50
<211> LENGTH: 11
<212> TYPE: PRT
<213> ORGANISM: Homo sapiens
<220> FEATURE:
<223> OTHER INFORMATION: Antibody 5

<400> SEQUENCE: 50

Gln Ser Tyr Asp Ser Ser Leu Ser Gly Trp Val
               5                  10

<210> SEQ ID NO 51
<211> LENGTH: 212
<212> TYPE: PRT
<213> ORGANISM: Homo sapiens
<220> FEATURE:
<223> OTHER INFORMATION: Full length Human IL-6

<400> SEQUENCE: 51

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 52
<211> LENGTH: 203
<212> TYPE: PRT
<213> ORGANISM: Homo sapiens
<220> FEATURE:
<223> OTHER INFORMATION: HIS FLAG tagged human IL-6

<400> SEQUENCE: 52

Met Gly Ser Ser His His His His His Asp Tyr Lys Asp Asp Asp
1               5                   10                  15

Asp Lys His Met Val Pro Pro Gly Glu Asp Ser Lys Asp Val Ala Ala
            20                  25                  30
```

```
Pro His Arg Gln Pro Leu Thr Ser Ser Glu Arg Ile Asp Lys Gln Ile
        35                  40                  45

Arg Tyr Ile Leu Asp Gly Ile Ser Ala Leu Arg Lys Glu Thr Cys Asn
 50                  55                  60

Lys Ser Asn Met Cys Glu Ser Ser Lys Glu Ala Leu Ala Glu Asn Asn
 65                  70                  75                  80

Leu Asn Leu Pro Lys Met Ala Glu Lys Asp Gly Cys Phe Gln Ser Gly
                 85                  90                  95

Phe Asn Glu Glu Thr Cys Leu Val Lys Ile Ile Thr Gly Leu Leu Glu
                100                 105                 110

Phe Glu Val Tyr Leu Glu Tyr Leu Gln Asn Arg Phe Glu Ser Ser Glu
            115                 120                 125

Glu Gln Ala Arg Ala Val Gln Met Ser Thr Lys Val Leu Ile Gln Phe
130                 135                 140

Leu Gln Lys Lys Ala Lys Asn Leu Asp Ala Ile Thr Thr Pro Asp Pro
145                 150                 155                 160

Thr Thr Asn Ala Ser Leu Leu Thr Lys Leu Gln Ala Gln Asn Gln Trp
                165                 170                 175

Leu Gln Asp Met Thr Thr His Leu Ile Leu Arg Ser Phe Lys Glu Phe
                180                 185                 190

Leu Gln Ser Ser Leu Arg Ala Leu Arg Gln Met
            195                 200

<210> SEQ ID NO 53
<211> LENGTH: 358
<212> TYPE: PRT
<213> ORGANISM: Homo sapiens
<220> FEATURE:
<223> OTHER INFORMATION: Soluble IL-6Ra

<400> SEQUENCE: 53

Met Leu Ala Val Gly Cys Ala Leu Leu Ala Ala Leu Leu Ala Ala Pro
 1               5                  10                  15

Gly Ala Ala Leu Ala Pro Arg Arg Cys Pro Ala Gln Glu Val Ala Arg
                 20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
 50                  55                  60

Pro Ala Ala Gly Ser His Pro Ser Arg Trp Ala Gly Met Gly Arg Arg
 65                  70                  75                  80

Leu Leu Leu Arg Ser Val Gln Leu His Asp Ser Gly Asn Tyr Ser Cys
                 85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
```

```
                195                 200                 205
Gln Gly Cys Gly Ile Leu Gln Pro Asp Pro Ala Asn Ile Thr Val
        210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
        260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp
        355

<210> SEQ ID NO 54
<211> LENGTH: 395
<212> TYPE: PRT
<213> ORGANISM: Homo sapiens
<220> FEATURE:
<223> OTHER INFORMATION: FLAG HIS tagged sIL-6Ra

<400> SEQUENCE: 54

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
        100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
        130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
        180                 185                 190

Cys Val Ala Ser Ser Val Gly Ser Lys Phe Ser Lys Thr Gln Thr Phe
        195                 200                 205
```

```
Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Val Gln Asp Lys Gly Arg Ala Asp Pro Ala Phe Leu
        355                 360                 365

Tyr Lys Val Val Gly Ala Ala Asp Tyr Lys Asp Asp Asp Lys Ala
    370                 375                 380

Ala His His His His His His His His His
385                 390                 395

<210> SEQ ID NO 55
<211> LENGTH: 561
<212> TYPE: PRT
<213> ORGANISM: Homo sapiens
<220> FEATURE:
<223> OTHER INFORMATION: Hyper IL-6

<400> SEQUENCE: 55

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
        50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175
```

```
Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
        275                 280                 285

Val Val Gln Leu Arg Ala Gln Glu Glu Phe Gly Gln Gly Glu Trp Ser
    290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Gly Ser Arg Arg Gly Ser Cys Gly Leu Gly Gly Gly
        355                 360                 365

Gly Ser Gly Gly Gly Gly Ser Gly Thr Pro Val Pro Gly Glu Asp
    370                 375                 380

Ser Lys Asp Val Ala Ala Pro His Arg Gln Pro Leu Thr Ser Ser Glu
385                 390                 395                 400

Arg Ile Asp Lys Gln Ile Arg Tyr Ile Leu Asp Gly Ile Ser Ala Leu
                405                 410                 415

Arg Lys Glu Thr Cys Asn Lys Ser Asn Met Cys Glu Ser Ser Lys Glu
            420                 425                 430

Ala Leu Ala Glu Asn Asn Leu Asn Leu Pro Lys Met Ala Glu Lys Asp
        435                 440                 445

Gly Cys Phe Gln Ser Gly Phe Asn Glu Glu Thr Cys Leu Val Lys Ile
    450                 455                 460

Ile Thr Gly Leu Leu Glu Phe Glu Val Tyr Leu Glu Tyr Leu Gln Asn
465                 470                 475                 480

Arg Phe Glu Ser Ser Glu Glu Gln Ala Arg Ala Val Gln Met Ser Thr
                485                 490                 495

Lys Val Leu Ile Gln Phe Leu Gln Lys Lys Ala Lys Asn Leu Asp Ala
            500                 505                 510

Ile Thr Thr Pro Asp Pro Thr Thr Asn Ala Ser Leu Leu Thr Lys Leu
        515                 520                 525

Gln Ala Gln Asn Gln Trp Leu Gln Asp Met Thr Thr His Leu Ile Leu
    530                 535                 540

Arg Ser Phe Lys Glu Phe Leu Gln Ser Ser Leu Arg Ala Leu Arg Gln
545                 550                 555                 560

Met

<210> SEQ ID NO 56
<211> LENGTH: 598
<212> TYPE: PRT
<213> ORGANISM: Homo sapiens
<220> FEATURE:
```

<223> OTHER INFORMATION: FLAG HIS tagged Hyper IL-6

<400> SEQUENCE: 56

```
Met Leu Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
            35                  40                  45

Gly Val Glu Pro Glu Asp Asn Ala Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
            340                 345                 350

Ser Leu Pro Gly Ser Arg Arg Gly Ser Cys Gly Leu Gly Gly Gly
            355                 360                 365

Gly Ser Gly Gly Gly Gly Ser Gly Thr Pro Val Pro Pro Gly Glu Asp
            370                 375                 380

Ser Lys Asp Val Ala Ala Pro His Arg Gln Pro Leu Thr Ser Ser Glu
385                 390                 395                 400

Arg Ile Asp Lys Gln Ile Arg Tyr Ile Leu Asp Gly Ile Ser Ala Leu
```

```
                        405                 410                 415
Arg Lys Glu Thr Cys Asn Lys Ser Asn Met Cys Glu Ser Ser Lys Glu
                420                 425                 430

Ala Leu Ala Glu Asn Asn Leu Asn Leu Pro Lys Met Ala Glu Lys Asp
                435                 440                 445

Gly Cys Phe Gln Ser Gly Phe Asn Glu Glu Thr Cys Leu Val Lys Ile
                450                 455                 460

Ile Thr Gly Leu Leu Glu Phe Glu Val Tyr Leu Glu Tyr Leu Gln Asn
465                 470                 475                 480

Arg Phe Glu Ser Ser Glu Glu Gln Ala Arg Ala Val Gln Met Ser Thr
                485                 490                 495

Lys Val Leu Ile Gln Phe Leu Gln Lys Lys Ala Lys Asn Leu Asp Ala
                500                 505                 510

Ile Thr Thr Pro Asp Pro Thr Thr Asn Ala Ser Leu Leu Thr Lys Leu
                515                 520                 525

Gln Ala Gln Asn Gln Trp Leu Gln Asp Met Thr Thr His Leu Ile Leu
                530                 535                 540

Arg Ser Phe Lys Glu Phe Leu Gln Ser Ser Leu Arg Ala Leu Arg Gln
545                 550                 555                 560

Met Lys Gly Gly Arg Ala Asp Pro Ala Phe Leu Tyr Lys Val Val Gly
                565                 570                 575

Ala Ala Asp Tyr Lys Asp Asp Asp Lys Ala Ala His His His His His
                580                 585                 590

His His His His His His
                595

<210> SEQ ID NO 57
<211> LENGTH: 468
<212> TYPE: PRT
<213> ORGANISM: Homo sapiens
<220> FEATURE:
<223> OTHER INFORMATION: Full length transmembrane IL-6Ra

<400> SEQUENCE: 57

Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
                35                  40                  45

Gly Val Glu Pro Glu Asp Asn Ala Thr Val His Trp Val Leu Arg Lys
                50                  55                  60

Pro Ala Ala Gly Ser His Pro Ser Arg Trp Ala Gly Met Gly Arg Arg
65              70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
                115                 120                 125

Asn Val Val Cys Glu Trp Gly Pro Arg Ser Thr Pro Ser Leu Thr Thr
                130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175
```

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
            195                 200                 205

Gln Gly Cys Gly Ile Leu Gln Pro Asp Pro Ala Asn Ile Thr Val
210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
            260                 265                 270

Leu Gln His His Cys Val Ile His Asp Ala Trp Ser Gly Leu Arg His
            275                 280                 285

Val Val Gln Leu Arg Ala Gln Glu Glu Phe Gly Gln Gly Glu Trp Ser
290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
            355                 360                 365

Val Ala Gly Gly Ser Leu Ala Phe Gly Thr Leu Leu Cys Ile Ala Ile
370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
450                 455                 460

Phe Phe Pro Arg
465

<210> SEQ ID NO 58
<211> LENGTH: 918
<212> TYPE: PRT
<213> ORGANISM: Homo sapiens
<220> FEATURE:
<223> OTHER INFORMATION: Human gp130

<400> SEQUENCE: 58

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

-continued

```
Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ser Gly Leu Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
                180                 185                 190

Asn Ile Glu Val Trp Val Glu Ala Glu Asn Ala Leu Gly Lys Val Thr
            195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
                260                 265                 270

Pro Pro Glu Asp Thr Ala Ser Thr Arg Ser Ser Phe Thr Val Gln Asp
                275                 280                 285

Leu Lys Pro Phe Thr Glu Tyr Val Phe Arg Ile Arg Cys Met Lys Glu
            290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
                340                 345                 350

Thr Leu Pro Pro Phe Glu Ala Asn Gly Lys Ile Leu Asp Tyr Glu Val
            355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
                420                 425                 430

Phe Pro Lys Asp Asn Met Leu Trp Val Glu Trp Thr Thr Pro Arg Glu
            435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480
```

```
Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
            515                 520                 525

Lys Val Gly Lys Asn Glu Ala Val Leu Glu Trp Asp Gln Leu Pro Val
        530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
            595                 600                 605

Thr Thr Pro Lys Phe Ala Gln Gly Glu Ile Glu Ala Ile Val Val Pro
        610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
            675                 680                 685

Thr Asp Val Ser Val Val Glu Ile Glu Ala Asn Asp Lys Lys Pro Phe
        690                 695                 700

Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
        850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895
```

```
Thr Asp Glu Gly Met Pro Lys Ser Tyr Leu Pro Gln Thr Val Arg Gln
                900                 905                 910

Gly Gly Tyr Met Pro Gln
            915

<210> SEQ ID NO 59
<211> LENGTH: 183
<212> TYPE: PRT
<213> ORGANISM: Homo sapiens
<220> FEATURE:
<223> OTHER INFORMATION: Mature IL-6

<400> SEQUENCE: 59

Val Pro Pro Gly Glu Asp Ser Lys Asp Val Ala Ala Pro His Arg Gln
1               5                   10                  15

Pro Leu Thr Ser Ser Glu Arg Ile Asp Lys Gln Ile Arg Tyr Ile Leu
            20                  25                  30

Asp Gly Ile Ser Ala Leu Arg Lys Glu Thr Cys Asn Lys Ser Asn Met
        35                  40                  45

Cys Glu Ser Ser Lys Glu Ala Leu Ala Glu Asn Asn Leu Asn Leu Pro
    50                  55                  60

Lys Met Ala Glu Lys Asp Gly Cys Phe Gln Ser Gly Phe Asn Glu Glu
65                  70                  75                  80

Thr Cys Leu Val Lys Ile Ile Thr Gly Leu Leu Glu Phe Glu Val Tyr
                85                  90                  95

Leu Glu Tyr Leu Gln Asn Arg Phe Glu Ser Ser Glu Glu Gln Ala Arg
            100                 105                 110

Ala Val Gln Met Ser Thr Lys Val Leu Ile Gln Phe Leu Gln Lys Lys
        115                 120                 125

Ala Lys Asn Leu Asp Ala Ile Thr Thr Pro Asp Pro Thr Thr Asn Ala
    130                 135                 140

Ser Leu Leu Thr Lys Leu Gln Ala Gln Asn Gln Trp Leu Gln Asp Met
145                 150                 155                 160

Thr Thr His Leu Ile Leu Arg Ser Phe Lys Glu Phe Leu Gln Ser Ser
                165                 170                 175

Leu Arg Ala Leu Arg Gln Met
            180
```

ANTIBODIES SPECIFIC FOR THE COMPLEX OF INTERLEUKIN-6 AND THE INTERLEUKIN-6 RECEPTOR

This application is a national phase filing and claims the benefit of Application No, PCT/GB2007/004534, filed Nov. 28, 2007, which claims the benefit of United States Provisional Application No. 60/861,705, filed Nov. 30, 2006, each of which are hereby incorporated by reference in their entirety for all purposes.

This invention relates to binding members, especially antibody molecules, which inhibit biological effects of IL-6. The binding members are useful for treatment of disorders associated with IL-6, including inflammatory diseases and tumours.

Interleukin 6 (IL-6) is a 26 kDa pleiotropic pro-inflammatory cytokine produced by a variety of cell types, including stimulated fibroblasts, monocytes and endothelial cells, which form the major source of IL-6 in vivo. Cells such as T cells, B cells, macrophages, keratinocytes, osteoblasts and several others can produce IL-6 on stimulation. IL-6 is also expressed from tumour cell lines and tumour cells e.g. cells from lung carcinoma, prostate cancer, myeloma, hypernephroma and cardiac myxoma (Kishimoto, T., Blood 74:1-10 (1989) and Smith P. C. et al. Cytokine and Growth factor Reviews 12:33-40 (2001)). Under non-inflammatory conditions, IL-6 is secreted from adipose tissue (Wallenius et al., Nat. Med. 8:75 (2002)).

The regulation of IL-6 expression depends on the cell type that is producing it. In multiple myeloma cells IL-6 appears to act in a positive feedback loop—stimulating the cells to grow as well as produce more IL-6 (Kawano et al. Nature 332:83 (1988) and Van Zaanen et al. J. Clin Invest. 98:1441-1448 (1996)). In other cell types IL-6 appears to inhibit the growth and activation of cells and may act as a negative regulator for some pro-inflammatory cytokines.

To initiate cell signalling, IL-6 binds with low affinity to a transmembrane receptor, IL-6 receptor alpha (also referred to as IL-6Rα, IL-6Ra, IL-6R, gp80 or CD126) to form a complex "IL-6:IL-6Ra". This complex binds to the gp130 signal receptor; IL-6Rα and gp130 together form a high affinity IL-6 binding site, and induce the formation of a hexamer composed of two copies each of IL-6, IL-6Ra and gp130 (Somers, W., et al 1997. 1.9 EMBO J. 16:989-997). The transmembrane and cytoplasmic domains of the IL-6Ra are not required for signal transduction, as IL-6Ra also exists as a soluble secreted form (sIL-6R or sIL-6Ra). The soluble receptor is produced either by differential splicing of the IL-6Ra message or by proteolytic shedding. sIL-6R is capable of forming a ligand-receptor complex with IL-6, "IL-6:sIL-6Ra". This complex can bind gp130 on cells and thereby initiate cell signalling in gp130 positive cells, even if those cells do not express IL-6Ra. Thus, sIL-6R has the potential to widen the repertoire of cells responsive to IL-6, and is thought to play an important role in IL-6-mediated inflammation (Jones, S. A et al. 2001. FASEB J. 15:43-58).

A crystal structure of human IL-6 ligand has been elucidated (Somers et al. EMBO J. (1997) 16:989-997). The crystal structure of the extracellular domain of human IL-6Ra (Varghese et al. Proc Nat Acad Sci (2002) 99:15959-15964), and the hexameric structure of IL-6/IL-6R/gp130 complex (Boulanger et al Science 300:2101-2104 (2003)), have also been resolved. These structures combined with mutagenesis studies have identified three sites on the surface of IL-6 which are involved in the functional activity of the IL-6 in complex with the various receptor components. Site 1 residues are involved in the interaction between IL-6 and IL-6Ra. Site 2 residues are involved in the interaction between IL-6 and the gp130 cytokine binding domain. The residues in Site 3 of IL-6 are involved in interacting with the Ig-like domain of the second gp130 in the hexameric complex. A fourth site on IL-6 has also been identified where IL-6 interacts with the second molecule of IL-6 in the hexameric IL-6/IL-6R/gp130 complex (Menziani et al (1997) Proteins: Structure Function and Genetics 29, 528).

Similar studies have been carried out on the extracellular domain of human IL-6Ra. This extracellular region has 3 domains D1 (P26-V112), D2 (P113-Q215), D3 (P216-M311). Although the Ig domain D1 has been shown to be dispensable for ligand recognition and signal initiation, it is implicated in receptor internalisation and protein stability. Domains D2 and D3 are Fibronectin type III domains and they form the cytokine binding domain. Structural studies have identified three "cluster" sites on this extracellular domain (Varghese et al. Proc Nat Acad Sci (2002) 99:15959-15964); Cluster 1 residues are predominantly involved in IL-6 ligand binding. Cluster 2 residues form part of the IL-6Ra dimerisation interface. These residues interfere with the formation of the IL-6R dimer and have a significant effect on IL-6 signalling but not on IL-6 binding. Cluster 3 residues on IL-6Ra are involved in the formation of the IL-6/IL-6R complex with gp130 to form the hexameric IL-6/IL-6Ra/gp130 complex.

A number of anti-IL-6 ligand monoclonal antibodies have been isolated. Mapping studies have been performed which show that these bind to different binding sites, as described above, on the surface of human IL-6 (Brakenhoff et al. J. Immunol. (1990) 145:561-568, Wijdenes et al. Mol. Immunol. (1991) 28:1183-1191, Brakenhoff et al. (1994) JBC 269: 86, Kalai et al. (1996) Eur J Biochem 238 714-723, Kalai et al. (1997) Blood 89:1319-1333).

A number of anti-IL-6Ra monoclonal antibodies have also been generated and their binding sites on the IL-6Ra mapped (Hirata et al. (1989) J. Immunol. 143:2900-2906, Kalai et al. (1996) Eur J Biochem 238 714-723, Kalai et al. (1997) Blood 89:1319-1333, Kalai et al. (1997) Eur J. Biochem 249:690-700).

IL-6 belongs to a family of cytokines, which includes Interleukin-11 (IL-11), ciliary neurotrophic factor (CNTF), Oncostatin M (OsM), Leukaemia Inhibitory Factor (LIF), cardiotrophin-like cytokine (CLC), and Cardiotrophin 1 (CT-1). Each of the members of this family has their own specific receptor alpha subunits and complexes with the common receptor subunit gp130. Targeted disruption of the gp130 gene is embryonically lethal (Ernst, M. and B. J. Jenkins. 2004. Trends Genet. 20:23-32 and Yoshida, K. et al 1996. Proc. Natl. Acad. Sci. USA 93:407-411). All members of the IL-6 family can induce the expression of acute phase proteins from hepatocytes.

IL-6 signalling involves tyrosine phosphorylation by JAK family kinases, and subsequent activation of two major intracellular signalling cascades, the SHP2/ERK MAPK and STAT1/3 pathways, leading to gene expression via NF-IL-6 and AP-1 (Ernst, M. & B. J. Jenkins. 2004. Trends Genet. 20:23-32, and Heinrich, P. C. et al. 2003. Biochem. J. 374:1-20).

IL-6 shows a wide spectrum of biological functions including, haematopoiesis, induction of acute phase responses, T cell activation, stimulation of antibody secretion, host defence against infection, myeloma cell and osteoclast activation (Choy, E. 2004. Rheum. Dis. Clin. North Am. 30:405-415 and Jones S A et al. FASEB J 15:43-58 (2001)). For a review of the effects of IL-6 see Kishimoto Arthritis Research & Therapy 2006 8:Supp 2/S2. IL-6 was originally identified as a B-cell differentiation factor generated by T cells (Hirano T et al. Nature (1986) 324:73-76) but has subsequently been identified as a potent activator and growth-promoting factor of many cell types. It induces the final maturation of B cells into antibody producing cells and is an essential accessory factor for T cell activation and proliferation. Studies have shown that IL-6 is involved in the activation of auto-reactive T lymphocytes and the proliferation and differentiation of cytotoxic T cells. IL-6 has been implicated in haematopoiesis as a cofactor causing the activation and differentiation of haemopoietic stem cells. The effect of IL-6 on the acute phase response is also well documented (For review see Moshage J. Pathol. (1997) 181:257-266). IL-6 induces a variety of acute phase proteins including fibrinogen, alpha-anti-chymotrypsin, serum amyloid A and C-reactive protein from human hepatocytes. Acute phase proteins control immune responses and inflammation and have effects on tissue remodelling. The serum level of IL-6 correlates well with that of C-reactive protein in variety of pathologies suggesting a causal role of IL-6 in the acute phase response. IL-6 has also been shown to be produced by osteoblasts and appears to be involved in osteoclast activation and bone resorption (Guillen, C. et al. 2004. Calcif. Tissue Int. 75:153-159, Tamura, T., et al. 1993. Proc. Natl. Acad. Sci. USA 90:11924-11928, Udagawa, N et al. 1995. J. Exp. Med. 182:1461-1468). Paradoxically it has been suggested that IL-6 not only has roles as a pro-inflammatory cytokine but can also, in certain circumstances and cell types, dampen the effects of other pro-inflammatory cytokines leading to a reduction in inflammation.

Because IL-6 has a variety of biological effects, the elevation of IL-6 has been implicated as a key cytokine in a variety of disease indications. The levels of circulating IL-6 have been shown to be elevated in diseases such as rheumatoid arthritis, Castleman's disease, Juvenile Idiopathic arthritis and Crohn's Disease (Nishimoto N, and Kishimoto T., Curr Op in Pharmaclogy (2004) 4:386-391). Because of this IL-6 has been implicated in driving the pathology in these inflammatory indications. Furthermore, a variety of tumor types have been shown to be stimulated by IL-6, including melanoma, renal cell carcinoma, Kaposi's sarcoma, ovarian carcinoma, lymphoma and leukemia, multiple myeloma, and prostate carcinoma (Keller E. T. et al. Front Biosci; 1:340-57 (1996)). Moreover increased circulating levels of IL-6 have been reported in several cancers. In some cancer indications elevated IL-6 levels has been used as prognostic indicators of the disease.

Because of the role of IL-6 in disease a variety of murine and chimaeric anti-human IL-6 monoclonal antibodies have been developed as potential therapies.

U.S. Pat. No. 5,856,135 describes a reshaped human antibody to IL-6, derived from a mouse monoclonal antibody "SK2".

JP-10-66582 reports a chimaeric antibody to IL-6, which is indicated as recognising the helix D region of IL-6 (site 1). WO2004/020633 (EP1536012) describes a human scFv antibody molecule to IL-6 isolated using phage display technology. The scFv is reported to have an affinity of 13 nM.

A murine anti-IL-6 antibody, elsilimomab (also known as B-E8) has been used to treat patients with Multiple myeloma (Bataille et al. Blood (1995) 86:685-691, Lu et al. Blood (1995) 68:3123-3131), renal cell carcinoma (Blay et al. Int J. Cancer 1997, 424-430 and rheumatoid arthritis (Wendling et al. J. Rheumatol. (1993). 20:259-262) and in improvements in certain diagnostic markers were seen in treated patients with all three diseases. BE-8 has also been used to treat HIV-positive patients with immunoblastic or polymorphic large cell lymphoma (Emilie et al. Blood 1994, 84:2472-2479) with relief of systemic symptoms (i.e. fever, sweats, cachexia) and suppression of spontaneous growth of the lymphoma in approximately 50% of patients.

However, the rapid clearance of this antibody and possible anaphylactic reactions due to the production of human anti-mouse antibodies (HAMA) to elsilimomab has limited its use in the clinic (Brochier J et al. Int. J. of Immunopharm. 1995, 17:41-48).

In general, clinical use of murine monoclonal antibodies is limited, as such antibodies frequently induce HAMA. HAMA directed against the Fc part of the mouse immunoglobulin are often produced, resulting in rapid clearance of anti-IL-6 mAb and possible anaphylactic reaction (Brochier J et al. Int. J. of Immunopharm. 1995, 17:41-48). It is also known that the pharmacokinetics of mouse antibodies in humans is different from human antibodies having shorter half lives and increased rates of clearance.

To reduce the immunogenicity of murine antibodies in humans, chimeric antibodies with mouse variable regions and human constant regions have been constructed. A chimeric human-mouse anti-IL-6 antibody cCLB8 (known as CNTO 328) has been used to treat patients with multiple myeloma (van Zaanen et al. J. Clin Invest 1996, 98:1441-1448 and van Zaanen et al. Brit. Journal. Haematology 1998, 102:783), with disease stabilisation seen in the majority of patients.

However, although chimeric antibodies are less immunogenic than murine MAbs, human anti-chimeric antibody (HACAs) responses have been reported (Bell and Kamm, (2000) Aliment. Phamacol. Ther. 14, 501-514).

The positive effect of inhibiting IL-6 signalling in cancer and inflammatory diseases has also been further highlighted by the use of a humanised anti-IL-6Ra antibody Tocilizumab (also known as hPM-1, MRA and Actemra). This is a humanised version of the murine anti-IL6Ra antibody PM-1. Treatment of patients with this antibody has proved effective in a number of diseases including rheumatoid arthritis, Juvenile idiopathic arthritis, Crohn's disease, Myeloproliferative disorder, Castleman's disease and Systemic lupus erythematosus (Mihara et al. Expert Opinion on Biological Therapy. 2005 5:683-90).

This invention provides isolated binding members that bind the IL-6:IL-6Ra complex formed by IL-6 and IL-6Ra, and do not bind either IL-6 or IL-6Ra alone. Described herein are binding members that bind the complex formed by IL-6 and sIL-6Ra (IL-6:sIL-6Ra) and do not bind IL-6 or sIL-6Ra alone. Thus, binding members of the invention do not bind IL-6 that is not complexed with IL-6Ra, e.g. sIL-6Ra. Nor do binding members of the invention bind IL-6Ra, e.g. sIL-6Ra, unless the IL-6Ra is complexed with IL-6.

We recognised that a binding member that could bind the complex formed by IL-6 and IL-6Ra and not bind IL-6 nor IL-6Ra alone could offer significant advantages as compared with binding members that bind IL-6 and/or IL-6Ra outside the IL-6:IL-6Ra complex. As described in Example 1, we invented a novel method to select binding members for a complex formed between a ligand and a receptor (here, IL-6 and IL-6Ra), wherein the binding members do not bind the ligand (here, IL-6) nor the receptor (here, IL-6Ra) alone (i.e. when the ligand and receptor are not bound to one another). We thus isolated for the first time antibodies that specifically bind IL-6:IL-6Ra. As described elsewhere herein, this complex represents the mechanism by which IL-6 exerts its effects in vivo. Binding and inhibition of this complex (e.g. inhibition of the complex binding to gp130) is a mechanism by which the biological activity of IL-6 may be directly inhibited, and offers the possibility of achieving inhibition in a more specific manner than by targeting IL-6 or its receptor alone. Binding members of the invention have numerous useful applications, for example in the fields of therapeutic treatment and diagnosis, and offer new and unique advantages over the prior art, since all previously known antibodies bind IL-6 or IL-6Ra outside the IL-6:IL-6Ra complex.

Because of the mechanism of IL-6 signalling, for IL-6 to be active it has to form a complex with IL-6Ra (soluble or membrane bound). The circulating levels of IL-6 are significantly lower than circulating levels of sIL-6Ra in disease (Desgeorges et al. J. Rheumatol (1997) 24:1510; Yokota et al. Arth & Rheum (2005) 52:818). As IL-6 binds to IL-6R with nanomolar affinity, the concentration of IL-6:IL-6R complex will be approximately 10-fold less than the concentrations of free IL-6 and free IL-6Ra. Therefore, a binding member targeting the IL-6:IL-6Ra complex, e.g. targeting IL-6:sIL-6Ra, has a much lower amount of target to neutralise and hence potentially less binding member i.e. a lower dose, may be required to inhibit it.

This has significant advantages in that the amount of drug to be manufactured for each dose to patients may be lower. Also, if the dose of an anti-IL-6 therapeutic is lower then there may be significant advantages in that the low dose facilitates sub-cutaneous injections as well as intra-venous (i.v.) injections. It is well known to those skilled in the art that sub-cutaneous dosing may be limited by the amount of antibody required per dose. This is due to the sub-cutaneous injections being limited by the volume that can be injected at one site in the skin. Sub-cutaneous injection volumes of 1.2 ml or less are typically utilised. As it may be increasingly difficult to formulate an antibody for sub-cutaneous injection at concentrations greater than 50 mg/ml, doses above 100 mg via this route usually require multiple injections and more discomfort for the patient.

A lower dose anti-IL-6:IL-6Ra therapy may therefore have significant advantages over either an anti-IL-6 ligand or an anti-IL-6Ra therapy which could require higher doses.

Having a lower dose anti-IL-6:IL-6Ra therapeutic may also require a lower "loading" dose of binding member to inhibit all the active IL-6 complexed with IL-6Ra, compared with the systemic free (uncomplexed) IL-6 and sIL-6Ra which are at significantly higher concentrations.

Soluble IL-6Ra, and IL-6:sIL-6Ra, may be present in systemic circulation of individuals, and may be present at elevated levels in individuals having an IL-6-related disorder. Many pathological effects of IL-6, i.e. its involvement in disease, are believed to be mediated by the soluble-IL-6:IL-6Ra complex. However, IL-6 also has beneficial biological effects in vivo, such as in mediating the body's response to infection. Certain beneficial effects of IL-6 effects may be mediated via binding to transmembrane IL-6Ra more than via sIL-6Ra. Since the IL-6:sIL-6Ra complex is formed in the systemic circulation, whereas the transmembrane IL-6:IL-6Ra complex forms on the cell surface and is rapidly internalised into the cell, IL-6:sIL-6Ra may be more available than the transmembrane complex to binding by binding members of the invention. Accordingly, binding members of the invention may have greater specificity for inhibiting pathological effects of IL-6 rather than beneficial effects of IL-6, as compared with binding members that bind IL-6 or IL-6Ra outside the IL-6:IL-6Ra complex.

Any suitable method may be used to determine whether a binding member binds IL-6:IL-6Ra (e.g. IL-6:sIL-6Ra), IL-6 and/or IL-6Ra (e.g. sIL-6Ra). Methods of determining and quantifying binding of binding members are known in the art and examples are described in detail herein—see the Materials and Methods section. The methods described in the Examples are exemplified for use with antibody molecules but may be adapted for use with any binding member. A suitable method may comprise quantifying binding of a binding member (i) to IL-6 alone (not complexed with IL-6Ra), (ii) to IL-6Ra alone e.g. sIL-6Ra (not complexed with IL-6), and (iii) to IL-6:IL-6Ra e.g. IL-6:sIL-6Ra. As noted elsewhere herein, hyper IL-6 may be used in assays to represent IL-6:IL-6Ra. Thus, a binding member of the invention may bind hyper IL-6 and not bind IL-6 or IL-6Ra alone. As exemplified herein, a method may comprise an ELISA to determine specificity of antibody molecules. In the Examples the level of binding was measured as Europium counts, however any suitable reporter system or detectable label may be employed. Further, a method may comprise quantifying binding to (iv) a control antigen, wherein the control antigen is an antigen to which the binding member does not bind, i.e. a negative control. A binding member may be said to bind IL-6 if the level of binding to IL-6 is at least 2.5 fold greater than the level of binding to the control antigen. A binding member may be said to bind IL-6R if the level of binding to IL-6R is at least 2.5 fold greater than the level of binding to the control antigen. A binding member may be said to bind IL-6:IL-6Ra if the level of binding to IL-6:IL-6Ra is at least 2.5 fold greater than the level of binding to the control antigen.

The level of binding to (iii) relative to binding to (i) and (ii) as quantified for a binding member indicates the degree of specificity of the binding member for the IL-6:IL-6Ra complex relative to IL-6 and IL-6Ra alone. For example, the level of binding to IL-6:IL-6Ra may be at least 2.5 fold greater than the level of binding to IL-6 and IL-6Ra respectively. The level of binding may be at least 5-, 10-, 15-, 20-, 25-, 30-, 45-, 50-, 55-, 60-, 65-, 70-, 75-, 80-, 80-, 85-, or at least 90-fold greater.

As described in more detail below, binding members according to the invention have been shown to neutralise IL-6:IL-6Ra with high potency. Neutralisation means inhibition of a biological activity of IL-6:IL-6Ra (e.g. IL-6:sIL-6Ra). Binding members of the invention may neutralise one or more activities of IL-6:IL-6Ra. The inhibited biological activity is typically IL-6:IL-6Ra (e.g. IL-6:sIL-6Ra) binding to gp130. In accordance with the invention, binding of IL-6:IL-6Ra to gp130 may be inhibited.

Inhibition in biological activity may be partial or total. Binding members may inhibit IL-6:IL-6Ra biological activity by 100%, or at least 95%, at least 90%, at least 85%, at least 80%, at least 75%, at least 70%, at least 60%, or at least 50% of the activity in absence of the binding member.

Neutralising potency of a binding member may be determined. Potency is normally expressed as an $IC_{50}$ value, in nM unless otherwise stated. In functional assays, $IC_{50}$ is the concentration of a binding member that reduces a biological response by 50% of its maximum. In ligand-binding studies, $IC_{50}$ is the concentration that reduces receptor binding by 50% of maximal specific binding level. Thus, in an assay measuring inhibition of IL-6:IL-6Ra complex binding to gp130, $IC_{50}$ is the concentration that reduces binding to gp130 by 50% of maximal specific binding level. $IC_{50}$ may be calculated by plotting % of maximal biological response as a function of the log of the binding member concentration, and using a software program, such as Prism (GraphPad) to fit a sigmoidal function to the data to generate $IC_{50}$ values. Potency may be determined or measured using one or more assays known to the skilled person and/or as described or referred to herein.

Neutralisation of IL-6:IL-6Ra activity by a binding member in an assay described herein indicates that the binding member binds and neutralises IL-6:IL-6Ra. Other methods that may be used for determining binding of a binding member to IL-6:IL-6Ra include ELISA, Western blotting, immunoprecipitation, affinity chromatography and biochemical assays.

A binding member of the invention may inhibit binding of the IL-6:IL-6Ra complex to gp130. Inhibition of IL-6:IL-6Ra binding to gp130 may be measured in an assay, e.g. an HTRF® (Homogeneous Time-Resolved Fluorescence) assay for the inhibition of FLAG HIS tagged Hyper IL-6 binding to recombinant human gp130 Fc, as described in the Materials and Methods section of the Examples. IC50 values in the HTRF assay as described herein are for a final concentration of 1 nM complex and 1 nM gp130. A shown in the Examples herein, a binding member of the invention may have a neutralising potency or IC50 of not more than 700 nM in an HTRF assay with a final concentration of 1 nM IL-6:IL-6Ra complex and a final concentration of 1 nM gp130, e.g. not more than 30, 25, 20, 15, 10, 5, 1.5, 1, 0.8 or 0.7 nM (see for example Table 2).

A binding member of the invention may comprise an antibody molecule, e.g. a human antibody molecule. The binding member normally comprises an antibody VH and/or VL domain. VH and VL domains of binding members are also provided as part of the invention. Within each of the VH and VL domains are complementarity determining regions, ("CDRs"), and framework regions, ("FRs"). A VH domain comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. Examples of antibody VH and VL domains and CDRs according to the present invention are as listed in the appended sequence listing that forms part of the present disclosure.

All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs. Typically binding members of the invention are monoclonal antibodies.

A binding member of the invention may comprise an antigen-binding site within a non-antibody molecule, normally provided by one or more CDRs e.g. a set of CDRs in a non-antibody protein scaffold, as discussed further below.

As described in more detail in the Examples, we isolated five antibody molecules, numbered Antibodies 1 to 5. Sequences of each of antibodies 1 to 5 are provided in the appended sequence listing, wherein for each antibody the following sequences are shown in order: nucleotide sequence encoding VH domain; amino acid sequence of VH domain; VH CDR1 amino acid sequence, VH CDR2 amino acid sequence; VH CDR3 amino acid sequence; nucleotide sequence encoding VL domain; amino acid sequence of VL domain; VL CDR1 amino acid sequence; VL CDR2 amino acid sequence; and VL CDR3 amino acid sequence, respectively.

A binding member of the invention may comprise one or more CDRs as described herein, e.g. a CDR3, and optionally also a CDR1 and CDR2 to form a set of CDRs. The CDR or set of CDRs may be a CDR or set of CDRs of any of antibodies 1 to 5, or may be a variant thereof as described herein.

The invention provides binding members comprising an HCDR1, HCDR2 and/or HCDR3 of any of antibodies 1 to 5 and/or an LCDR1, LCDR2 and/or LCDR3 of any of antibodies 1 to 5, e.g. a set of CDRs of any of antibodies 1 to 5.

The binding member may comprise a set of VH CDRs of one of these antibodies. Optionally it may also comprise a set of VL CDRs of one of these antibodies, and the VL CDRs may be from the same or a different antibody as the VH CDRs.

A VH domain comprising a set of HCDRs of any of antibodies 1 to 5, and/or a VL domain comprising a set of LCDRs of any of antibodies 1 to 5, are also provided by the invention.

Typically, a VH domain is paired with a VL domain to provide an antibody antigen-binding site, although as discussed further below a VH or VL domain alone may be used to bind antigen. The antibody 1 VH domain may be paired with the antibody 1 VL domain, so that an antibody antigen-binding site is formed comprising both the antibody 1 VH and VL domains. Analogous embodiments are provided for the other VH and VL domains disclosed herein. In other embodiments, the antibody 1 VH is paired with a VL domain other than the antibody VL. Light-chain promiscuity is well established in the art. Again, analogous embodiments are provided by the invention for the other VH and VL domains disclosed herein.

Thus, the VH of any of antibodies 1 to 5 may be paired with the VL of any of antibodies 1 to 5.

A binding member may comprise a set of H and/or L CDRs of any of antibodies 1 to 5 with one or more amino acid mutations within the disclosed set of H and/or L CDRs. The mutation may be an amino acid substitution, deletion or insertion. Thus for example there may be one or more amino acid substitutions within the disclosed set of H and/or L CDRs. For example, there may be up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene segment sequences. Thus, the framework may be germlined, whereby one or more residues within the framework are changed to match the residues at the equivalent position in the most similar human germline framework. A binding member of the invention may be an isolated human antibody molecule having a VH domain comprising a set of HCDRs in a human germline framework.

Normally the binding member also has a VL domain comprising a set of LCDRs, e.g. in a human germline framework.

A germlined VL domain may or may not be germlined at the Vernier residue, but is normally not.

The 3' ggt codon, and corresponding Glycine residue, shown in the nucleotide and amino acid sequences for the VL domains of Antibodies 1, 2, 3, 4, and 5 respectively were included in the expressed scFv and IgG sequences of these antibodies. The C terminal Glycine residue is residue 109 in SEQ ID NO: 7, residue 114 in SEQ ID NO: 17, residue 112 in SEQ ID NOs: 27 and 47 and residue 113 in SEQ ID NO: 37. Using Kabat numbering, these positions correspond to Kabat residue 108. The origin of this residue and its encoding triplet ggt is explained below.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL domain and CL domain. After splicing, the C terminal Glycine (corresponding to Kabat residue 108) is encoded by the last base (g) of the VL domain framework 4 sequence and the first two bases (gt) of the CL domain. The Glycine residue at Kabat residue 108 may be considered to be the C terminal residue of the VL domain of the antibody molecule.

A binding member of the invention may be one which competes for binding to IL-6:IL-6Ra, e.g. IL-6:sIL-6Ra, with any binding member which (i) binds IL-6:IL-6Ra e.g. IL-6: sIL-6Ra and (ii) comprises a binding member, VH and/or VL domain, CDR e.g. HCDR3, and/or set of CDRs disclosed herein.

Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein. Thus, a further aspect of the present invention provides a binding member comprising a human antibody antigen-binding site that competes with an antibody molecule, for example especially an antibody molecule comprising a VH and/or VL domain, CDR e.g. HCDR3 or set of CDRs of any of antibodies 1 to 5 for binding to IL-6:IL-6Ra e.g. IL-6:sIL-6Ra.

In further aspects, the invention provides an isolated nucleic acid which comprises a sequence encoding a binding member, VH domain and/or VL domain according to the present invention, and methods of preparing a binding member, a VH domain and/or a VL domain of the invention, which comprise expressing said nucleic acid under conditions to bring about production of said binding member, VH domain and/or VL domain, and recovering it.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of binding, inhibiting and/or neutralising IL-6:IL-6Ra e.g. IL-6:sIL-6Ra complex, including methods of treatment of the human or animal body by therapy.

Binding members of the invention are useful for treating disorders associated with IL-6, as described in detail elsewhere herein.

Binding members according to the invention may be used in a method of treatment or diagnosis, such as a method of treatment (which may include prophylactic treatment) of a disease or disorder in the human or animal body (e.g. in a human patient), which comprises administering to said patient an effective amount of a binding member of the invention. Conditions treatable in accordance with the present invention include any in which IL-6 plays a role, as discussed in detail elsewhere herein.

These and other aspects of the invention are described in further detail below.

Terminology

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

IL-6 and IL-6 Receptor

IL-6 is interleukin 6.

The full length amino acid sequence of human IL-6 is SEQ ID NO: 51. This sequence is cleaved in vivo to remove an N-terminal leader peptide, and the mature sequence of IL-6 is SEQ ID NO: 59. The mature sequence represents the in vivo circulating IL-6, which is the target antigen for therapeutic and in vivo diagnostic applications as described herein. Accordingly, IL-6 referred to herein is normally mature human IL-6, unless otherwise indicated by context.

IL-6 receptor a, IL-6Ra, is the receptor for interleukin 6. IL-6Ra is also known as IL-6Rα, IL-6Ra, IL-6R and CD126. IL-6Ra exists in vivo in a transmembrane form and in a soluble form. References to IL-6Ra may be transmembrane IL-6Ra and/or soluble IL-6Ra unless otherwise indicated by context.

An amino acid sequence of human soluble IL-6Ra (sIL-6R, sIL-6Ra) is SEQ ID NO: 51. An amino acid sequence of human transmembrane IL-6Ra is SEQ ID NO: 57.

IL-6 binds IL-6Ra to form a complex, IL-6:IL-6Ra. IL-6: IL-6Ra may also be referred to herein as "the antigen". The complex may be either soluble (with sIL-6Ra) or membrane bound (with transmembrane IL-6Ra). When the IL-6Ra is the soluble form, the complex is designated IL-6:sIL-6Ra. References to IL-6:IL-6Ra may include IL-6 complexed with transmembrane or soluble IL-6Ra, unless otherwise indicated by context.

Aspects of the invention as described herein are detailed in the Examples with reference to sIL-6Ra and IL-6:sIL-Ra, and IL-6:sIL-6Ra is a target antigen of interest, e.g. for in vivo applications since this complex may be bound in the systemic circulation by binding members of the invention. However, binding members of the invention may also or instead bind the complex formed by IL-6 and transmembrane IL-6Ra, which is also a target antigen of interest for in vivo applications.

Hyper IL-6 is a fusion protein in which IL-6 is covalently linked to sIL-6Ra via a linker peptide. The sequence of hyper IL-6 as used in the Examples is SEQ ID NO: 55.

IL-6, IL-6Ra (e.g. sIL-6Ra) and hyper IL-6 may be conjugated to a detectable label, such as HIS FLAG, e.g. for use in assays as described herein. For example, a fusion protein comprising IL-6, IL-6Ra (e.g. sIL-6Ra) or hyper IL-6 conjugated to a HIS FLAG sequence may be used. A sequence of HIS FLAG tagged human IL-6 is SEQ ID NO: 52. A sequence of HIS FLAG tagged human sIL-6Ra is SEQ ID NO: 53. A sequence of HIS FLAG tagged hyper IL-6 is SEQ ID NO: 56.

gp130 gp130 is a receptor for the IL-6:IL-6Ra complex. Cloning and characterisation of gp130 is reported in Hibi et al, Cell 63:1149-1157 1990. A sequence of human gp130 is SEQ ID NO: 58.

Binding Member

This describes one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds, such as fibronectin or cytochrome B etc. [1, 2, 3], or by randomising or mutating amino acid residues of a loop within a protein scaffold to confer binding specificity for a desired target. Scaffolds for engineering novel binding sites in proteins have been reviewed in detail by Nygren et al. [3]. Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [4]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from *S. aureus*, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners).

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [5], and updates thereof. A number of academic and commercial on-line resources are available to query this database. For example, see ref. [6] and the associated on-line resource, currently at the web address of http://www.bioinf.org.uk/abs/simkab.html.

By CDR region or CDR, it is intended to indicate the hypervariable regions of the heavy and light chains of the immunoglobulin as defined by Kabat et al. 1991 [7], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody [refs. 8, 9, 10, 11, 12, 13, 14, 15].

Antibody Molecule

This describes an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but that they have been able to be isolated or obtained by purification from natural sources, or else obtained by genetic recombination, or by chemical synthesis, and that they can then contain unnatural amino acids as will be described later. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies and minibodies. Antibody molecules and methods for their construction and use are described in [16].

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel [17]. Phage display, another established technique for generating binding members has been described in detail in many publications, such as Kontermann & Dubel [17] and WO92/01047 (discussed further below), and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160, 6,521,404.

Transgenic mice in which the mouse antibody genes are inactivated and functionally replaced with human antibody genes while leaving intact other components of the mouse immune system, can be used for isolating human antibodies [18]. Humanised antibodies can be produced using techniques known in the art such as those disclosed in for example WO91/09967, U.S. Pat. No. 5,585,089, EP592106, U.S. Pat. No. 565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [19] or Krebs et al. [20].

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [21, 22, 23], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [24, 25]; (viii) bispecific single chain Fv dimers (PCT/US92/09965) and (ix) "diabodies", multivalent or multispecific fragments constructed by gene fusion (WO94/13804; [26]). Fv, scFv or diabody molecules may be stabilized by the incorporation of disulphide bridges linking the VH and VL domains [27]. Minibodies comprising a scFv joined to a CH3 domain may also be made [28]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Qui et al. [29] described antibody molecules containing just two CDRs linked by a framework region. CDR3 from the VH or VL domain was linked to the CDR1 or CDR2 loop of the other domain. Linkage was through the C terminus of the selected CDR1 or CDR2 to the N terminus of the CDR3, via a FR region. Qui et al. selected the FR region having the fewest hydrophobic patches. The best combination for the antibody tested was found to be VL CDR1 linked by VH FR2 to VH CDR3 (VHCDR1-VHFR2-VLCDR3). At a molecular weight of around 3 kDa, these antibody molecules offer advantages in terms of improved tissue penetration as compared with full immunoglobulins (approx. 150 kDa) or scFv (approx. 28 kDa).

Antibody fragments of the invention can be obtained starting from a any of the antibody molecules 1 to 5, by methods such as digestion by enzymes e.g. pepsin or papain and/or by cleavage of the disulfide bridges by chemical reduction.

In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain [23]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [30]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [31], e.g. prepared chemically or from hybrid hybridomas, or may be any of the bispecific antibody fragments mentioned above. These antibodies can be obtained by chemical methods [32, 33] or somatic methods [34, 35] but likewise and preferentially by genetic engineering techniques which allow the heterodimerization to be forced and thus facilitate the process of purification of the antibody sought [36]. Examples of bispecific antibodies include those of the BiTE™ technology in which the binding domains of two antibodies with different specificity can be used and directly linked via short flexible peptides. This combines two antibodies on a short single polypeptide chain.

Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected using phage display (WO94/13804) from libraries. If one arm of the diabody is to be kept constant, for instance, with a specificity directed against IL-6:IL-6Ra, then a library can be made where the other arm is varied and an antibody of appropriate specificity selected. Bispecific whole antibodies may be made by alternative engineering methods as described in Ridgeway et al., 1996 [37].

Various methods are available in the art for obtaining antibodies against IL-6:IL-6Ra.

The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [38] or to the technique of preparation from hybridomas described by Köler and Milstein [39].

Monoclonal antibodies can be obtained, for example, from an animal cell immunized against IL-6:IL-6Ra, e.g. using hyper IL-6, or one of its fragments containing the epitope recognized by said monoclonal antibodies. Suitable fragments and peptides or polypeptides comprising them are described herein, and may be used to immunise animals to generate antibodies against IL-6:IL-6Ra e.g. IL-6:sIL-6Ra. Said IL-6:sIL-6Ra, or one of its fragments, can especially be produced according to the usual working methods, by genetic recombination starting with a nucleic acid sequence contained in a DNA sequence coding for hyper IL-6 or fragment thereof, by peptide synthesis starting from a sequence of amino acids comprised in the peptide sequence of the IL-6:sIL-6Ra and/or fragment thereof.

The monoclonal antibodies can, for example, be purified on an affinity column on which IL-6:sIL-6Ra, or hyper IL-6, or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

Antigen-binding Site

This describes the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope.

An antibody antigen-binding site may be provided by one or more antibody variable domains. An antibody antigen-binding site may comprise an antibody light chain variable region (VL) and an antibody heavy chain variable region (VH).

Isolated

This refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-IL-6:IL-6Ra (e.g. anti-IL-6:sIL-6Ra) antibody molecules also form part of the invention. For example, such preparations may be mixtures of antibodies with full-length heavy chains and heavy chains lacking the C-terminal lysine, with various degrees of glycosylation and/or with derivatized amino acids, such as cyclisation of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 5, e.g. from 1 to 4, including 1 to 3, or 1 or 2, or 3 or 4, amino acid substitutions may be made in the CDR and/or VH or VL domain.

DETAILED DESCRIPTION OF THE INVENTION

As noted above, a binding member in accordance with the present invention modulates and may neutralise a biological activity of IL-6 and/or IL-6Ra e.g. sIL-6Ra. A binding member of the present invention may be subjected to potency optimisation, to further improve its neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated.

Nevertheless, high potency binding members may be obtained without optimisation. As demonstrated herein, high potency binding members may be obtained directly from an initial screen e.g. a biochemical neutralization assay.

A "potency optimized" binding member refers to a binding member with an optimized potency of neutralization of a particular activity or downstream function of IL-6 and/or IL-6Ra e.g. sIL-6Ra. Assays and potencies are described in more detail elsewhere herein.

Potency-optimized and non-optimized binding members are aspects of the invention, as well as methods for potency optimization from a selected binding member. The present invention thus allows the skilled person to generate binding members having high potency.

As described herein, Antibody 1 had a neutralising potency (IC50) of less than 700 nM in an HTRF® (Homogeneous Time-Resolved Fluorescence) assay for the inhibition of FLAG HIS tagged Hyper IL-6 binding to recombinant human gp130 Fc. Thus, a binding member comprising the Antibody 1 set of CDRs may exhibit an IC50 of less than 700 nM in this assay. Variants of Antibody 1, having one or more substitutions, deletions or insertions within the Antibody 1 set of CDRs, may be of the same potency or more potent than Antibody 1.

As described herein, Antibody 2 had a neutralising potency (IC50) of less than 1.5 nM in an HTRF® (Homogeneous Time-Resolved Fluorescence) assay for the inhibition of FLAG HIS tagged Hyper IL-6 binding to recombinant human gp130 Fc. Thus, a binding member comprising the Antibody 2 set of CDRs may exhibit an IC50 of less than 1.5 nM in this assay. Variants of Antibody 2, having one or more substitutions, deletions or insertions within the Antibody 2 set of CDRs, may be of the same potency or more potent than Antibody 2.

As described herein, Antibody 3 had a neutralising potency (IC50) of less than 25 nM in an HTRF® (Homogeneous Time-Resolved Fluorescence) assay for the inhibition of FLAG HIS tagged Hyper IL-6 binding to recombinant human gp130 Fc. Thus, a binding member comprising the Antibody 3 set of CDRs may exhibit an IC50 of less than 25 nM in this assay. Variants of Antibody 3, having one or more substitutions, deletions or insertions within the Antibody 3 set of CDRs, may be of the same potency or more potent than Antibody 3.

As described herein, Antibody 4 had a neutralising potency (IC50) of less than 30 nM in an HTRF® (Homogeneous Time-Resolved Fluorescence) assay for the inhibition of FLAG HIS tagged Hyper IL-6 binding to recombinant human gp130 Fc. Thus, a binding member comprising the Antibody 4 set of CDRs may exhibit an IC50 of less than 30 nM in this assay. Variants of Antibody 4, having one or more substitutions, deletions or insertions within the Antibody 4 set of CDRs, may be of the same potency or more potent than Antibody 4.

As described herein, Antibody 5 had a neutralising potency (IC50) of less than 0.8 nM in an HTRF® (Homogeneous Time-Resolved Fluorescence) assay for the inhibition of FLAG HIS tagged Hyper IL-6 binding to recombinant human gp130 Fc. Thus, a binding member comprising the Antibody 5 set of CDRs may exhibit an IC50 of less than 0.8 nM in this assay. Variants of Antibody 5, having one or more substitutions, deletions or insertions within the Antibody 5 set of CDRs, may be of the same potency or more potent than Antibody 5.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a said selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Further aspects of the invention relate generally to isolation or selection of a binding member from a plurality of binding members, wherein the selected or isolated binding member binds a complex formed by a first entity and a second entity and does not bind the first or second entity alone.

The plurality of binding members may be a library of binding members, as described above. Binding members are defined and described in more detail elsewhere herein. Conveniently, as is common in libraries, each binding member in the plurality of binding members may be associated with genetic information encoding it, allowing recovery of the genetic information when a binding member is selected.

In one aspect, the invention is a method of selecting a binding member from a plurality of binding members, wherein the binding member binds a complex formed by a first entity and a second entity and does not bind the first or second entity alone, wherein the method comprises:
(i) exposing the plurality of binding members to the first entity, under conditions allowing binding of binding members to the first entity;
(ii) exposing the plurality of binding members to the complex formed by the first entity and the second entity, under conditions allowing binding of binding members to the complex;
(iii) isolating the complex on a solid support to which the second entity is attached; and
(iv) recovering one or more binding members bound to the complex.

Thus, the method may select, from the plurality of binding members, a population of binding members that bind to the complex.

The method may optionally further comprise amplifying the one or more recovered binding members to produce a plurality of binding members, e.g. by:
(v) amplifying genetic information encoding the one or more recovered binding members; and (vi) expressing the genetic information to produce a plurality of binding members.

The method may comprise repeating steps (i) to (iv) above, for subsequent rounds of selection. Subsequent rounds of selection may thus further select from a population of binding members that bind the complex, and may negatively select against non-specific binding members or binding members that bind to the first or second entity alone.

Advantageously, the orientation in which the complex is attached to the support (i.e. whether attached via the first entity or via the second entity) may be alternated in subsequent rounds of selection. Thus, the method may optionally further comprise:

(vii) exposing the plurality of binding members to the second entity, under conditions allowing binding of binding members to the second entity;
(viii) exposing the plurality of binding members to the complex formed by the first entity and the second entity, under conditions allowing binding of binding members to the complex;
(ix) isolating the complex on a solid support to which the first entity is attached; and
(x) recovering one or more binding members bound to the complex.

Steps (i)-(vi) above may then be repeated, and multiple of rounds of selection may be performed, wherein the entity attached to the support is alternated. Thus, the method may comprise a first round of selection in which the first entity is attached to the support, and a second round of selection in which the second entity is attached to the support, then a third round of selection in which the first entity is attached to the support, and so on for subsequent rounds until the desired number of rounds of selection has been completed, thus alternating the orientation in which the complex is isolated on the support. This alternation of orientation in binding the complex to the support contributes to specific selection of binding members that bind the complex and do not bind the first or second entity alone. The alternation may particularly assist in selecting against binding members that bind the first or second entity alone.

The support to which the entity is attached may for example be a bead. Conveniently, paramagnetic beads may be used, which are readily recoverable from solution.

The entity attached to the support may be attached directly or indirectly. For example, the support may comprise or be coated with a binding member that binds the entity. Alternatively, the entity may be tagged, i.e. covalently attached to a tag such as a peptide, for attachment to the support, wherein the support comprises or is coated with a binding member that binds the tag. For example, a polypeptide may be linked to a heterologous peptide tag e.g. a FLAG tag, and may be attached to a solid support by means of an antibody molecule or other binding member that binds the tag, e.g. an anti-FLAG antibody. The binding member that binds the tag may conveniently be coated on to the support by means of a streptavidin: biotin complex, e.g. a biotinylated binding member may be attached to a streptavidin-coated support, e.g. streptavidin-coated beads.

Conveniently, in each round of selection, one entity may be linked to a tag for attachment to the support, while the other entity is not linked to the tag (the other entity may be untagged, or may be linked to a different tag). Thus, in a first round of selection the second entity may be linked to a tag for attachment to the support, while the first entity is not linked to the tag, and in the second round of selection the first entity may be linked to the tag while the second entity is not. Use of the same tag for attachment of the first and second entity to the support in alternate rounds of selection conveniently allows the same type of support to be used in each round.

The first and/or second entity and the complex are normally provided in solution. However, in some cases the first and/or second entity may be on a surface, e.g. presented on a cell surface, so that the complex is formed on the surface, and the method may then comprise exposing the plurality of binding members in solution to cells expressing the first and/or second entity on the cell surface. Methods using cells are suitable for example where one or both of the first and second entities are transmembrane proteins, or membrane-associated proteins. However, an alternative is to use soluble portions of such proteins, e.g. an extracellular domain or portion of an extracellular domain may be used in the method, allowing the polypeptide to be provided in solution.

Complex may be formed by exposing the first entity to the second entity such that the first and second entity associate to form a complex. In each round of selection, the entity that is not to be attached to the support is normally provided at a concentration in excess of the entity that is to be attached to the support, e.g. at least a two fold molar excess. This ensures that substantially all the entity that is to be attached to the support is present in complexed form, minimising the amount of uncomplexed entity that is recovered on the support, and thereby minimising undesired recovery of binding member that binds the entity in uncomplexed form. An alternative is to expose the binding members to a pre-formed complex, e.g. a complex in which the first and second entity are covalently bound to one another. For example, where the first and second entities are polypeptides, a fusion protein comprising the first entity and second entity may be used, e.g. wherein the first and second entity are linked via a peptide tag. However, there are advantages to forming the complex by exposing the first entity to the second entity, since this represents the in vivo situation and avoids anomalies in conformation or epitope formation caused by covalent linkage of the first and second entity in the complex, if covalent linkage in the complex is non physiological.

Step (i) and step (ii) may be performed sequentially (step (i) then (ii)) or simultaneously. For example, binding members may be exposed to the first and then the second entity, or to the first and second entity simultaneously, wherein the first entity is at a concentration in excess of the second entity, e.g. at least two fold molar excess, and wherein the first and second entity form the complex.

An advantage of performing step (i) before step (ii) is that binding members are exposed to the first entity before being exposed to the complex, and therefore binding members that bind the first entity alone can be bound in the initial step, reducing the probability of these binding members binding to the complex in step (ii). The situation is analogous for steps (viii) and (iv), except that the first and second entities are swapped round.

Attachment of the second entity to the support may take place before step (ii), or in step (ii) or step (iii). For example, step (iii) may comprise exposing the complex to a support that binds the second entity, e.g. binds a tag attached to the second entity. The situation is analogous for steps (ix) and (x) in relation to attachment of the first entity to the support.

Isolated complexes may be washed to remove unbound binding members, and binding member bound to the complex may thus be recovered on the support from the plurality of binding members.

Methods may further comprise additional assays (e.g. ELISA, where the selected binding members are antibody molecules) to confirm that selected binding members bind the complex and do not bind the first or second entity alone, and/or to further select binding members that have desired properties such as greater specificity for the complex.

In one example the invention is a method of selecting a binding member from a plurality of binding members, wherein the binding member binds a complex formed by a first entity and a second entity and does not bind the first or second entity alone, wherein the method comprises:
providing the first and second entity, one of which is linked to a tag for attachment to a solid support ("tagged entity") and one of which not linked to the tag ("untagged entity");
(i) exposing the plurality of binding members to the untagged entity, under conditions allowing binding of binding members to the untagged entity;
(ii) exposing the plurality of binding members and the untagged entity to the tagged entity, wherein the untagged entity is at a concentration at least two-fold greater than the concentration of the tagged entity, such that the tagged entity forms a complex with the untagged entity, thereby exposing the plurality of binding members to the complex, under conditions allowing binding of binding members to the complex;
(iii) isolating the complex on a solid support to which the tagged entity is attached; and
(iv) recovering one or more binding members bound to the complex.

The method may optionally further comprise:
(v) amplifying genetic information encoding the one or more recovered binding members; and
(vii) expressing the genetic information to produce a plurality of binding members.

The method may then further comprise repeating steps (i) to (iv) for one or more subsequent rounds of selection. Advantageously, the orientation in which the complex is attached to the support may be alternated in subsequent rounds. Thus, if the first entity is tagged in round 1, the second entity is tagged in round 2, then the first entity tagged in round 3, and so on. As described above, use of the same tag for the first and second entity in alternate rounds of selection conveniently allows the same type of support to be used in each round i.e. a support comprising or coated with a binding member that binds the tag. Optionally, however, the first and second entities may both be tagged, and a different type of support used to isolate the complex in alternate rounds of selection. Thus, the "untagged entity" may optionally be linked to tag, provided that it is not the same tag that is linked to the tagged entity.

The first and second entities are typically organic molecules, normally biological molecules that associate to form a complex. Examples include ligand:receptor complexes formed by a ligand and a receptor, enzyme:substrate complexes formed by an enzyme and a substrate of the enzyme; and antibody:antigen complexes formed by an antibody molecule and an antigen to which the antibody molecule binds. The first and/or second entity may be a polypeptide, and thus the method may comprise selecting a binding member that binds a complex formed by a first polypeptide and a second polypeptide and does not bind the first or second polypeptide alone.

The first and second entities may be the same or different. Typically the first and second entities are different, e.g. different organic or biological molecules, e.g. different polypeptides. Thus, the method may comprise selecting a binding member that binds a complex in which two different entities are associated, e.g. wherein the complex is a heterodimer.

An epitope bound by binding members of the invention is formed when the first and second entities form a complex. For example, the epitope may comprise a part of the first entity and a part of the second entity, e.g. may comprise one or more amino acids from the first polypeptide and one or more amino acids from the second polypeptide. Alternatively, the epitope may be only on one entity, and may be present or exposed only when that entity is complexed with the other entity, as a result of a conformational change in the entity when it forms the complex.

In methods of the invention, ability to bind IL-6:IL-6Ra (e.g. IL-6:sIL-6Ra) may be further tested, also ability to compete with a binding member e.g. an antibody molecule 1 to 5 (e.g. in scFv format and/or IgG format, e.g. IgG1), for binding to IL-6:IL-6Ra e.g. IL-6:sIL-6Ra, may be determined. Ability to neutralize IL-6:IL-6Ra (e.g. IL-6:sIL-6Ra) may be tested, as discussed further elsewhere herein.

A binding member according to the present invention may bind IL-6:IL-6Ra e.g. IL-6:sIL-6Ra with the affinity of one of antibodies 1 to 5, e.g. scFv or IgG1, or with an affinity that is better.

A binding member according to the present invention may neutralise a biological activity of IL-6:IL-6Ra (e.g. IL-6:sIL-6Ra) with the potency of one of antibodies 1 to 5 e.g. scFv or IgG1, or with a potency that is better.

Binding affinity and neutralization potency of different binding members can be compared under appropriate conditions.

Variants of the VH and VL domains and CDRs of the present invention, including those for which amino acid sequences are set out herein, and which can be employed in binding members of the invention can be obtained by means of methods of sequence alteration or mutation and screening for antigen binding members with desired characteristics. Examples of desired characteristics include but are not limited to:
Increased binding affinity for antigen relative to known antibodies which are specific for the antigen
Increased neutralization of an antigen activity relative to known antibodies which are specific for the antigen if the activity is known
Specified competitive ability with a known antibody or ligand to the antigen at a specific molar ratio
Ability to immunoprecipitate complex
Ability to bind to a specified epitope
   Linear epitope, e.g. peptide sequence identified using peptide-binding scan as described herein, e.g. using peptides screened in linear and/or constrained conformation
   Conformational epitope, formed by non-continuous residues
   Ability to modulate a new biological activity of IL-6:IL-6Ra (e.g. IL-6:sIL-6Ra) or downstream molecule.
Such methods are also provided herein.

Variants of antibody molecules disclosed herein may be produced and used in the present invention. Following the lead of computational chemistry in applying multivariate data analysis techniques to the structure/property-activity relationships [40] quantitative activity-property relationships of antibodies can be derived using well-known mathematical techniques, such as statistical regression, pattern recognition and classification [41, 42, 43, 44, 45, 46]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [47, 48]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [47, 48].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [49] using any freely available or commercial package, such as WAM [50]. A protein visualisation and analysis software package, such as Insight II (Accelrys, Inc.) or Deep View [51] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IL-6 and/or IL-6Ra (e.g. sIL-6Ra) and/or for any other desired property.

Variable domain amino acid sequence variants of any of the VH and VL domains whose sequences are specifically disclosed herein may be employed in accordance with the present invention, as discussed.

Variants of VL domains of the invention, and binding members or antibody molecules comprising them, include VL domains in which Glycine is not present at Kabat residue 108, e.g. where Kabat residue 108 is a different residue or is deleted. For example, an antibody molecule, such as an antibody molecule lacking a constant domain, e.g. an scFv, may comprise a VL domain having a VL domain sequence or variant thereof as described herein, in which Glycine at Kabat residue 108 an amino acid residue other than Glycine or is deleted.

A further aspect of the invention is an antibody molecule comprising a VH domain that has at least 60, 70, 80, 85, 90, 95, 98 or 99% amino acid sequence identity with a VH domain of any of antibodies 1 to 5 shown in the appended sequence listing, and/or comprising a VL domain that has at least 60, 70, 80, 85, 90, 95, 98 or 99% amino acid sequence identity with a VL domain of any of antibodies 1 to 5 shown in the appended sequence listing. Algorithms that can be used to calculate % identity of two amino acid sequences include e.g. BLAST [52], FASTA [53], or the Smith-Waterman algorithm [54], e.g. employing default parameters.

Particular variants may include one or more amino acid sequence alterations (addition, deletion, substitution and/or insertion of an amino acid residue).

Alterations may be made in one or more framework regions and/or one or more CDRs. The alterations normally do not result in loss of function, so a binding member comprising a thus-altered amino acid sequence may retain an ability to bind and/or neutralize IL-6 and/or IL-6Ra (e.g. sIL-6Ra). It may retain the same quantitative binding and/or neutralizing ability as a binding member in which the alteration is not made, e.g. as measured in an assay described herein. The binding member comprising a thus-altered amino acid sequence may have an improved ability to bind and/or neutralize IL-6 and/or IL-6Ra (e.g. sIL-6Ra).

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [55]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired IL-6:IL-6Ra (e.g. IL-6:sIL-6Ra) binding and neutralizing properties in a binding member of the invention. Additionally, D-amino acids and analogues have been shown to have different pharmacokinetic profiles compared with standard L-amino acids, owing to in vivo degradation of polypeptides having L-amino acids after administration to an animal e.g. a human, meaning that D-amino acids are advantageous for some in vivo applications.

Novel VH or VL regions carrying CDR-derived sequences of the invention may be generated using random mutagenesis of one or more selected VH and/or VL genes to generate mutations within the entire variable domain. Such a technique is described by Gram et al. [56], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [57] and Schier et al. [58].

All the above-described techniques are known as such in the art and the skilled person will be able to use such techniques to provide binding members of the invention using routine methodology in the art.

A further aspect of the invention provides a method for obtaining an antibody antigen-binding site for IL-6:IL-6Ra, e.g. IL-6:sIL-6Ra, the method comprising providing by way of addition, deletion, substitution or insertion of one or more amino acids in the amino acid sequence of a VH domain set out herein a VH domain which is an amino acid sequence variant of the VH domain, optionally combining the VH domain thus provided with one or more VL domains, and testing the VH domain or VH/VL combination or combinations to identify a binding member or an antibody antigen-binding site for IL-6:IL-6Ra, e.g. IL-6:sIL-6Ra and optionally with one or more desired properties, e.g. ability to neutralize IL-6 and/or IL-6Ra (e.g. sIL-6Ra) activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [59] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [60], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for IL-6:IL-6Ra, e.g. IL-6:sIL-6Ra, is provided, which method comprises:
(a) providing a starting repertoire of nucleic acids encoding a VH domain which either include a CDR3 to be replaced or lack a CDR3 encoding region;
(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;
(c) expressing the nucleic acids of said product repertoire;
(d) selecting a binding member for IL-6:IL-6Ra, e.g. IL-6:sIL-6Ra; and
(e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for IL-6:IL-6Ra, e.g. IL-6:sIL-6Ra.

For example, one or more of the antibody 1 to 5 HCDR1, HCDR2 and HCDR3 or the antibody 1 to 5 set of HCDRs may be employed, and/or one or more of the antibody 1 to 5 LCDR1, LCDR2 and LCDR3 or the antibody 1 to 5 set of LCDRs may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind IL-6:IL-6Ra, e.g. IL-6:sIL-6Ra.

This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al, ibid. [59]

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG4. IgG1 is advantageous, due to its effector function and ease of manufacture. Any synthetic or other constant region variant that has these properties and stabilizes variable regions may also be useful in the present invention.

Binding members of the invention may be labelled with a detectable or functional label. Thus, a binding member or antibody molecule can be present in the form of an immunoconjugate so as to obtain a detectable and/or quantifiable signal. An immunoconjugates may comprise an antibody molecule of the invention conjugated with detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation,
- enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;
- dyes;
- fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and Cis Bio-international),
- chemoluminescent labels or chemiluminescers, such as isoluminol, luminol and the dioxetanes;
- bio-luminescent labels, such as luciferase and luciferin;
- sensitizers;
- coenzymes;
- enzyme substrates;
- radiolabels including but not limited to bromine77, carbon14, cobalt57, fluorine8, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;
- particles, such as latex or carbon particles; metal sol; crystallite; liposomes; cells, etc., which may be further labelled with a dye, catalyst or other detectable group;
- molecules such as biotin, digoxygenin or 5-bromodeoxyuridine;
- toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA mentioned above can be used for the radioelements which can be used in diagnosis. It is likewise possible to perform labelling with sodium125 by the chloramine T method [61] or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety).

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety.

The present invention provides a method comprising causing or allowing binding of a binding member as provided herein to IL-6:IL-6Ra, e.g. IL-6:sIL-6Ra. As noted, such binding may take place in vivo, e.g. following administration of a binding member, or nucleic acid encoding a binding member, or it may take place in vitro, for example in ELISA, Western blotting, immunocytochemistry, immunoprecipitation, affinity chromatography, and biochemical or cell-based assays, such as a TF-1 proliferation assay.

The present invention also provides for measuring levels of antigen directly, by employing a binding member according to the invention for example in a biosensor system. For instance, the present invention comprises a method of detecting and/or measuring binding to IL-6:IL-6Ra, e.g. IL-6:sIL-6Ra, comprising, (i) exposing said binding member to IL-6: IL-6Ra, e.g. IL-6:sIL-6Ra and (ii) detecting binding of said binding member to IL-6:IL-6Ra, e.g. IL-6:sIL-6Ra, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IL-6:IL-6Ra, e.g. IL-6:sIL-6Ra, may be determined. Quantitation may be related to the amount of the antigen in a test sample, which may be of diagnostic interest. Screening for IL-6:IL-6Ra, e.g. IL-6:sIL-6Ra, binding and/or the quantitation thereof may be useful, for instance, in screening patients for diseases or disorders referred to herein and/or any other disease or disorder involving aberrant IL-6 and/or IL-6Ra (e.g. sIL-6Ra) expression and/or activity. The levels of IL-6:IL-6Ra (e.g. IL-6:sIL-6Ra) may be used as a measure of the level of IL-6 in a sample.

A number of diseases are associated with increased levels of IL-6. IL-6 levels are a useful diagnostic and/or prognostic indicator for various disorders, for example cancers associated with increased levels of IL-6, and inflammatory and/or autoimmune diseases, as described elsewhere herein.

A diagnostic or prognostic method of the invention may comprise (i) obtaining a tissue or fluid sample from a subject, (ii) exposing said tissue or fluid sample to one or more binding members of the present invention; and (iii) detecting bound IL-6:IL-6Ra, e.g. IL-6:sIL-6Ra, as compared with a control sample, wherein an increase in the amount of IL-6: IL-6Ra (e.g. IL-6:sIL-6Ra) binding as compared with the control may indicate an aberrant level of expression or activity of IL-6 and/or IL-6Ra (e.g. sIL-6Ra). Tissue or fluid samples to be tested include blood, serum, urine, biopsy material, tumours, or any tissue suspected of containing aberrant IL-6:IL-6Ra (e.g. IL-6:sIL-6Ra) levels. Subjects testing positive for aberrant IL-6:IL-6Ra (e.g. IL-6:sIL-6Ra) levels or activity may also benefit from the treatment methods disclosed later herein.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to IL-6:IL-6Ra, e.g. IL-6:sIL-6Ra, with any binding member defined herein, e.g. any of antibodies 1 to 5, e.g. in IgG1 format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which IL-6:sIL-6Ra is immobilized to a plate and a first tagged or labelled binding member along with one or more other untagged or unlabelled binding members is added to the plate. As described elsewhere herein, hyper IL-6 may be used to represent IL-6:IL-6Ra and/or IL-6:sIL-6Ra in assays such as ELISA. Presence of an untagged binding member that competes with the tagged binding member is observed by a decrease in the signal emitted by the tagged binding member.

For example, the present invention includes a method of identifying an IL-6:IL-6Ra binding compound (e.g. an IL-6: sIL-6Ra binding compound), comprising (i) immobilizing IL-6:IL-6Ra, e.g. IL-6:sIL-6Ra, to a support, (ii) contacting said immobilized IL-6:IL-6Ra, e.g. IL-6:sIL-6Ra, simultaneously or in a step-wise manner with at least one tagged or labelled binding member according to the invention and one or more untagged or unlabelled test binding compounds, and (iii) identifying a new IL-6:IL-6Ra binding compound, e.g. IL-6:sIL-6Ra binding compound, by observing a decrease in the amount of bound tag from the tagged binding member. Such methods can be performed in a high-throughput manner using a multiwell or array format. Such assays may be also be performed in solution. See, for instance, U.S. Pat. No. 5,814, 468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by binding member for IL-6:IL-6Ra (e.g. for IL-6:sIL-6Ra) which optionally may have optimized neutralizing and/or modulating characteristics. Such an epitope can be linear or conformational. A conformational epitope can comprise at least two different fragments of IL-6:IL-6Ra (e.g. of IL-6:sIL-6Ra), wherein said fragments are positioned in proximity to each other in the complex to form a conformational epitope which is recognized by an inhibitor of IL-6:IL-6Ra (e.g. IL-6:sIL-6Ra), such as an IL-6:IL-6Ra-binding member (e.g. an IL-6:sIL-6Ra-binding member). In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one, the present invention provides a nucleic acid that codes for a CDR or set of CDRs or VH domain or VL domain or antibody antigen-binding site or antibody molecule, e.g. scFv or IgG1, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. For a review, see for example Plückthun [62]. A common bacterial host is *E. coli*.

Expression in eukaryotic cells in culture is also available to those skilled in the art as an option for production of a binding member [63, 64, 65]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [66]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [67].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

There is evidence for involvement of IL-6 in a variety of disorders, as discussed elsewhere herein. The binding members of the present invention may therefore be used in a method of diagnosis or treatment of a disorder associated with IL-6. Such a disorder may for example be an inflammatory and/or autoimmune disorder such as for example, rheumatoid arthritis, osteoarthritis, cachexia, chronic obstructive pulmonary disease, Juvenile idiopathic arthritis, asthma, systemic lupus erythematosus, inflammatory bowel disease, Crohn's disease or atherosclerosis. A binding member of the present invention may also be used to treat a disorder such as a tumour and/or cancer.

Thus at least one binding member of the present invention may be used for modulating or treating at least one IL-6 related disease, in a patient, animal, organ, tissue or cell, including, but not limited to:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute-, allergic-, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis, sinusitis, idiopathic pulmonary fibrosis (IPF); sarcoidosis, farmer's lung and related diseases, adult respiratory distress syndrome, hypersensitivity pneumonitis, fibroid lung and idiopathic interstitial pneumonia;

(2) (bone and joints) rheumatoid arthritis, juvenile chronic arthritis, systemic onset juvenile arthritis, seronegative spondyloarthropathies (including ankylosing spondylitis, psoriatic arthritis and Reiter's disease), Behcet's disease, Siogren's syndrome and systemic sclerosis, gout, osteoporosis and osteoarthritis;

(3) (skin) psoriasis, atopical dermatitis, contact dermatitis and other eczmatous dermatoses, allergic contact dermatitis, seborrhoetic dermatitis, Lichen planus, scleroderma, Pemphigus, bullous pemphigoid, Epidermolysis bullosa, urticaria, angiodermas, vasculitides, erythemas, cutaneous eosinophilias, uveitis, Alopecia greata, allergic conjunctivitis and vernalvemal conjunctivitis;

(4) (gastrointestinal tract) gastric ulcer, Coeliac disease, proctitis, eosinopilic gastro-enteritis, mastocytosis, inflammatory bowel disease, Crohn's disease, ulcerative colitis, antiphospholipid syndrome)), food-related allergies which have effects remote from the gut, e.g., migraine, rhinitis and eczema;

(5) (other tissues and systemic disease) cachexia, multiple sclerosis, atherosclerosis, Acquired Immunodeficiency Syndrome (AIDS), mesangial proliferative glomerulonephritis, nephrotic syndrome, nephritis, glomerular nephritis, acute renal failure, hemodialysis, uremia, localised or discoid lupus erythematosus, systemic lupus erythematosus, Castleman's Disease, Hashimoto's thyroiditis, myasthenia gravis, type I diabetes, type B insulin-resistant diabetes, sickle cell anaemia, iridocyclitis/uveitis/optic neuritis, nephritic syndrome, eosinophilia fascitis, hyper IgE syndrome, systemic vasculitis/wegener's granulomatosis, orchitis/vasectomy reversal procedures, lepromatous leprosy, alcohol-induced hepatitis, sezary syndrome and idiopathic thrombocytopenia purpura; post-operative adhesions, nephrosis, systemic inflammatory response syndrome, sepsis syndrome, gram positive sepsis, gram negative sepsis, culture negative sepsis, fungal sepsis, neutropenic fever, acute pancreatitis, urosepsis, Graves disease, Raynaud's disease, antibody-mediatated cytotoxicity, type III hypersensitivity reactions, POEMS syndrome (polyneuropathy, organomegaly, endocrinopathy, monoclonal gammopathy, and skin changes syndrome), mixed connective tissue disease, idiopathic Addison's disease, diabetes mellitus, chronic active hepatitis, primary, biliary cirrhosis, vitiligo, post-MI (cardiotomy) syndrome, type IV hypersensitivity, granulomas due to intracellular organisms, Wilson's disease, hemachromatosis, alpha-I-antitrypsin deficiency, diabetic retinopathy, hashimoto's thyroiditis, hypothalamic-pituitary-adrenal axis evaluation, thyroiditis, encephalomyelitis, neonatal chronic lung disease, familial hematophagocytic lymphohistiocytosis, alopecia, radiation therapy (e.g., including but not limited to asthenia, anemia, cachexia, and the like), chronic salicylate intoxication, sleep apnea, obesity, heart failure, and meningococcemia;

(6) (allograft rejection) acute and chronic following, for example, transplantation of kidney, heart, liver, lung, pancreas, bone marrow, bone, small bowel, skin, cartilage and cornea; and chronic graft versus host disease;

(7) (malignant disease) leukemia, acute lymphoblastic leukemia (ALL), acute leukemia, T-cell, B-cell, or FAB ALL, chromic myelocytic leukemia (CML), acute myeloid leukemia (AML), chronic lymphocytic leukemia (CLL), hairy cell leukemia, myelodyplastic syndrome (MDS), any lymphoma, Hodgkin's disease, non-hodgkin's lymphoma, any malignant lymphoma, Burkitt's lymphoma, multiple myeloma, Kaposi's sarcoma, renal cell carcinoma, colorectal carcinoma, prostatic carcinoma, pancreatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia;
(8) Cystic fibrosis, stroke, re-perfusion injury in the heart, brain, peripheral limbs and other organs;
(9) Burn wounds, trauma/haemorrhage, ionizing radiation exposure, chronic skin ulcers;
(10) Reproductive Diseases (e.g. Disorders of ovulation, menstruation and implantation, pre-term labour, pre-eclampsia, endometriosis);
(11) (Infections) acute or chronic bacterial infection, acute and chronic parasitic or infectious processes, including bacterial, viral and fungal infections, HIV infection/HIV neuropathy, meningitis, hepatitis (A,B or C, or other viral hepatitis the like), septic arthritis, peritonitis, pneumonia, epiglottitis, *e. coli* 0157:h7, hemolytic uremic syndrome/thrombotic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, Lyme disease, influenza a, epstein-barr virus, vital-associated hemaphagocytic syndrome, viral encephalitis/aseptic meningitis, and the like.

Accordingly, the invention provides a method of treating an IL-6 related disorder, comprising administering to a patient in need thereof an effective amount of one or more binding members of the present invention alone or in a combined therapeutic regimen with another appropriate medicament known in the art or described herein.

Evidence for involvement of IL-6 in certain disorders is summarised elsewhere herein. In addition, the data presented herein further indicates that binding members of the invention can be used to treat such disorders, including preventative treatment and reduction of severity of the disorders. Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Thus, the binding members of the present invention are useful as therapeutic agents in the treatment of diseases or disorders involving IL-6, e.g. IL-6 expression and/or activity, especially aberrant expression/activity. A method of treatment may comprise administering an effective amount of a binding member of the invention to a patient in need thereof, wherein aberrant expression and/or activity of IL-6 is decreased. A method of treatment may comprise (i) identifying a patient demonstrating aberrant IL-6 levels or activity, for instance using the diagnostic methods described above, and (ii) administering an effective amount of a binding member of the invention to the patient, wherein aberrant expression and/or activity of IL-6, IL-6Ra and/or IL-6:IL-6Ra (e.g. IL-6:sIL-6Ra) is decreased. An effective amount according to the invention is an amount that decreases the aberrant expression and/or activity of IL-6 so as to decrease or lessen the severity of at least one symptom of the particular disease or disorder being treated, but not necessarily cure the disease or disorder.

The invention also provides a method of antagonising at least one effect of IL-6 comprising contacting with or administering an effective amount of one or more binding members of the present invention such that said at least one effect of IL-6 is antagonised. Effects of IL-6 that may be antagonised by the methods of the invention include IL-6:IL-6Ra (e.g. IL-6:sIL-6Ra) binding to its receptor gp130, and any downstream effects that arise as a consequence of this binding.

Accordingly, further aspects of the invention provide methods of treatment comprising administration of a binding member as provided, pharmaceutical compositions comprising such a binding member, and use of such a binding member in the manufacture of a medicament for administration, for example in a method of making a medicament or pharmaceutical composition comprising formulating the binding member with a pharmaceutically acceptable excipient. A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration, such as for example single domain antibody molecules (e.g. "Nanobodies™") etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of binding members will depend upon the intended route of delivery: for example, formulations for pulmonary delivery may consist of particles with physical properties that ensure penetration into the deep lung upon inhalation; topical formulations (e.g. for treatment of scarring, e.g. dermal scarring) may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [68].

Treatment may be given orally (such as for example single domain antibody molecules (e.g. "Nanobodies™")) by injection (for example, subcutaneously, intra-articular, intravenously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that treatment will not be restricted to use in the clinic. Therefore, subcutaneous injection using a needle-free device is also advantageous.

A composition may be administered alone or in combination with other treatments, either simultaneously or sequentially dependent upon the condition to be treated.

A binding member of the invention may be used as part of a combination therapy in conjunction with an additional medicinal component. Combination treatments may be used to provide significant synergistic effects, particularly the combination of a binding member of the invention with one or more other drugs. A binding member of the invention may be administered concurrently or sequentially or as a combined preparation with another therapeutic agent or agents, for the treatment of one or more of the conditions listed herein.

A binding member of the invention may be used as a chemosensitiser whereby it can increase therapeutic efficacy of cytotoxic agents, and may thus be provided for administration in combination with one or more cytotoxic agents, either simultaneously or sequentially. The binding member may also be used as a radio sensitiser whereby it can improve efficacy of radiation, and may thus be provided for administration in combination with radiation, either simultaneously or sequentially.

A binding member according to the present invention may be provided in combination or addition with one or more of the following agents:

a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to -33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig, HuMax Il-15 or Abatacept);

a modulator that inhibits osteoclast activity, for example an antibody to RANKL;

a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 and CXCR6 (for the C-X-C family) and $CX_3CR1$ for the $C-X_3-C$ family;

an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;

a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY x 1005;

a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY x 7195;

a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;

a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastro-protective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;

an anticholinergic agent, e.g. a muscarinic receptor (M1, M2, and M3) antagonist, such as atropine, hyoscine, glycopyrrrolate, ipratropium bromide, tiotropium bromide, oxitropium bromide, pirenzepine and telenzepine;

a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;

a chromone, e.g. sodium cromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors, such as a PPAR;

an immunoglobulin (Ig) or Ig preparation or an antagonist or antibody modulating Ig function, such as anti-IgE (e.g. omalizumab);

other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an antiviral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as a calcium channel blocker, beta-adrenoceptor blocker, angiotensin-converting enzyme (ACE) inhibitor, angiotensin-2 receptor antagonist; lipid lowering agent, such as a statin and/or fibrate; a modulator of blood cell morphology, such as pentoxyfylline; a thrombolytic and/or an anticoagulant, e.g. a platelet aggregation inhibitor;

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B.sub1.- and/or B.sub2.-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK.sub1. and/or NK.sub3. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2X7; (xxvii) an inhibitor of transcription factor activation, such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent or another tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IL-6 is associated.

For treatment of an inflammatory disease, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intra-muscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention can also be used in combination with an existing therapeutic agent for the treatment of cancer. Suitable agents to be used in combination include:

(i) antiproliferative/antineoplastic drugs and combinations thereof, as used in medical oncology, such as Gleevec (imatinib mesylate), alkylating agents (for example cisplatin, carboplatin, cyclophosphamide, nitrogen mustard, melphalan, chlorambucil, busulphan and nitrosoureas); antimetabolites (for example antifolates, such as fluoropyrimidines like 5-fluorouracil and tegafur, raltitrexed, methotrexate, cytosine arabinoside, hydroxyurea, gemcitabine and paclitaxel); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents, such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase, such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents, such as those which inhibit the effects of vascular endothelial growth factor (for example the anti-vascular endothelial cell growth factor antibody bevacizumab, compounds, such as those disclosed in International Patent Applications WO 97/22596, WO 97/30035, WO 97/32856 and WO 98/13354, each of which is incorporated herein in its entirety) and compounds that work by other mechanisms (for example linomide, inhibitors of integrin αvβ3 function and angiostatin);

(vi) vascular damaging agents, such as combretastatin A4 and compounds disclosed in International Patent Applications WO 99/02166, WO 00/40529, WO 00/41669, WO 01/92224, WO 02/04434 and WO 02/08213 (each of which is incorporated herein in its entirety);

(vii) antisense therapies, for example those which are directed to the targets listed above, such as ISIS 2503, an anti-ras antisense;

(viii) gene therapy approaches, including for example approaches to replace aberrant genes, such as aberrant p53 or aberrant BRCA1 or BRCA2, GDEPT (gene directed enzyme pro-drug therapy) approaches, such as those using cytosine deaminase, thymidine kinase or a bacterial nitroreductase enzyme and approaches to increase patient tolerance to chemotherapy or radiotherapy, such as multidrug resistance gene therapy; and (ix) immunotherapeutic approaches, including for example ex vivo and in vivo approaches to increase the immunogenicity of patient tumour cells, such as transfection with cytokines, such as interleukin 2, interleukin 4 or granulocyte macrophage colony stimulating factor, approaches to decrease T-cell energy, approaches using transfected immune cells, such as cytokine-transfected dendritic cells, approaches using cytokine-transfected tumour cell lines and approaches using anti-idiotypic antibodies.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art [69, 70]. Specific dosages indicated herein or in the Physician's Desk Reference (2003) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 μg to 1 g for systemic applications, and 1 μg to 1 mg for topical applications. An initial higher loading dose, followed by one or more lower doses, may be administered. Typically, the antibody will be a whole antibody, e.g. the IgG1 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

EXAMPLES

Example 1

Isolation of Antibodies to the Human IL-6/sIL-6R Complex from Naïve Phage Display Libraries Selections were carried out in solution using FLAG-tagged complex, and capturing using streptavidin coated paramagnetic beads treated with a biotinylated anti-FLAG monoclonal antibody. Formation of the IL-6/sIL-6R complex was done with only one of the two proteins (ligand or receptor) being FLAG tagged. All complex formed would therefore be captured in the same orientation on the anti-FLAG coated paramagnetic beads. To form the complex, a 2-fold excess of untagged protein was always added to the tagged material, so to minimise the amount of un-complexed tagged protein present in the selection. Subsequent rounds of selection were then completed using either the same FLAG-tagged protein throughout, or by alternating which protein was tagged, which in-turn alternated the orientation in which the complex was captured on the beads. To minimise the potential for the isolation of phage antibodies specific to either streptavidin or the anti FLAG monoclonal antibody, the libraries were first de-selected against the treated beads to remove such phage prior to the addition of the complex. ScFv that were able to bind to the IL-6/sIL-6R complex and inhibit its binding of gp130 were identified from the selection outputs using a biochemical assay involving the binding of gp130 to IL-6/sIL-6R covalently attached via a linker (Hyper IL-6). These neutralising scFv were then tested by phage ELISA to determine specificity to the IL-6/sIL-6R complex. To determine specificity, the samples were tested against the following FLAG tagged reagents immobilised on streptavidin-coated plates treated with biotinylated anti-FLAG monoclonal antibody: IL-6, sIL-6R, IL-6/sIL-6R complex consisting of FLAG tagged ligand and untagged receptor, IL-6/sIL-6R complex consisting of untagged ligand and FLAG tagged receptor, Hyper IL-6, and anti FLAG antibody treated plates alone. Complex specific clones were defined as those that bound to the hyper IL-6 and both forms of the complex, and did not bind to the ligand or receptor alone. Complex specific clones were re-formatted to IgG and re-evaluated in the gp130-Hyper-IL-6 biochemical assay. Specificity to the complex and not the individual components was also confirmed by ELISA and in a soluble binding assay.

Example 2

Hyper IL-6/gp130 Fc Binding HTRF® Assay (Crude Periplasmic Preparations)

Selection outputs were screened in a Hyper IL-6/gp130 Fc binding HTRF® (Homogeneous Time-Resolved Fluorescence) assay for the inhibition of FLAG HIS tagged Hyper IL-6 (In house HEK-EBNA expressed) binding to recombinant human gp130 Fc (R&D systems 671-GP). The detailed method is provided in the Materials and Methods section.

Example 3

Hyper IL-6/GP130 Fc Binding HTRF® Assay (Purified scFv Preparations)

ScFv that demonstrated a significant inhibitory effect as crude preparations were sequenced and produced as purified preparations. These samples were tested in a HTRF® assay for inhibition of binding of FLAG HIS tagged Hyper IL-6 to recombinant human gp130 Fc. A titration of scFv concentrations was used in order to establish the clone potency as measured by $IC_{50}$ values in the assay. The detailed method is provided in Materials and Methods. Potencies of purified scFv titrations in the Hyper IL-6/GP130 Fc binding HTRF® Assay are given in Table 2 with the corresponding IgG data.

Example 4

Phage ELISA Screen to Identify Complex Specific scFv

A phage ELISA screen was performed as described in Materials and Methods. ELISA for complex specific clones is shown in Table 1.

TABLE 1

Phage ELISA data to identification of IL-6/sIL-6R complex specific clones from the panel of scFv identified from selection outputs using the gp130-Hyper-IL-6 binding assay

| | Absorbance (450 nM) | | | | | |
|---|---|---|---|---|---|---|
| Clone | FLAG-IL-6 | FLAG-sIL-6R | Complex 1 | Complex 2 | HYPER-IL-6 | Anti-FLAG |
| Antibody 1 | 0.061 | 0.059 | 0.508 | 0.952 | 1.087 | 0.052 |
| Antibody 2 | 0.074 | 0.083 | 0.823 | 0.992 | 1.023 | 0.052 |
| Antibody 3 | 0.063 | 0.056 | 0.738 | 0.972 | 1.079 | 0.049 |
| Antibody 4 | 0.062 | 0.167 | 0.781 | 0.991 | 1.052 | 0.053 |
| Antibody 5 | 0.065 | 0.061 | 0.331 | 0.747 | 0.833 | 0.062 |

Complex 1: HIS FLAG IL-6/sIL-6R
Complex 2: IL-6/HIS FLAG sIL-6R

Example 5

Reformatting of scFv to IgG1

Clones were converted from scFv to IgG format by subcloning the $V_H$ and $V_L$ domains into vectors expressing whole antibody heavy and light chains respectively. The $V_H$ domain was cloned into a vector (pEU15.1) containing the human heavy chain constant domains and regulatory elements to express whole IgG heavy chain in mammalian cells. Similarly, the $V_L$ domain was cloned into a vector (pEU4.4) for the expression of the human light chain (lambda) constant domains and regulatory elements to express whole IgG light chain in mammalian cells. Vectors for the expression of heavy chains and light chains were originally described in ref. [71]. Cambridge Antibody Technology vectors have been engineered simply by introducing an OriP element. To obtain IgGs, the heavy and light chain IgG expressing vectors were transfected into EBNA-HEK293 mammalian cells. IgGs were expressed and secreted into the medium. Harvests were pooled and filtered prior to purification. The IgG was purified using Protein A chromatography. Culture supernatants are loaded on a column of appropriate size of Ceramic Protein A (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG [72]. The purified IgG were analysed for aggregation or degradation using SEC-HPLC and by SDS-PAGE.

Example 6

Hyper IL-6/Biotinylated GP130 Fc Binding HTRF® Assay

Purified IgG from positive clones identified from screening of crude periplasmic scFv and purified scFv were tested in a HTRF® assay for inhibition of binding of FLAG HIS tagged Hyper IL-6 binding to biotinylated recombinant human gp130 Fc. This assay was performed as for purified scFv (Example 3) with the following modifications. 6 nM biotinylated human recombinant gp130 Fc (10 µl/well) was used to give a final concentration of 1 nM of gp130Fc. For detection of binding, 2.598 nM anti-flag IgG labelled with cryptate and 10.8 nM or 12 nM of streptavidin XL$^{ent!}$ (CIS Bio International 611SAXLB) combined HTRF® reagents (10 µl/well) were used.

An IgG against an irrelevant antigen and anti-IL-6 monoclonal antibody (R&D systems MAB206) were included as controls in all assays. % deltaF, % specific binding and $IC_{50}$ values were calculated as previously described. $IC_{50}$ values for the complex specific clones are given in Table 2.

TABLE 2

Potency data for purified scFv and IgG in gp130-Hyper-IL-6 binding assay

| | Max inhibition (%)/$IC_{50}$ (nM) | |
|---|---|---|
| Clone | scFv* | IgG |
| Antibody 1 | maximum 42% | 654.6 |
| Antibody 2 | maximum 58% | 1.1 |
| Antibody 3 | maximum 66% | 20.8 |
| Antibody 4 | maximum 36% | 26.7 |
| Antibody 5 | maximum 83% | 0.7 |

*Where incomplete curves were obtained, result is given as the maximal % inhibition observed at the highest competitor concentration used.

Example 7

Specificity Testing of Anti-Complex IgG Using a HTRF® Soluble Assay

Purified IgG from positive clones identified from screening of crude periplasmic scFv and purified scFv, were tested in a HTRF® assay for binding to FLAG HIS tagged Hyper IL-6, FLAG HIS IL-6 and FLAG HIS sIL-6R.

Example data for binding of IgG of positive clones identified from screening of crude periplasmic scFv. Data shown in table 3 is expressed as % delta F at an IgG concentration of 1 nM (final assay concentration) and 20 nM of HIS FLAG protein (final assay concentration).

TABLE 3

Binding of complex specific IgG to IL-6, sIL-6R and Hyper IL-6 in a HTRF® soluble assay

| Clone | HIS FLAG Hyper IL-6 | HIS FLAG IL-6 ligand | HIS FLAG soluble IL-6 receptor | HIS FLAG irrelevant ligand | HIS FLAG irrelevant receptor |
|---|---|---|---|---|---|
| Antibody 1 | 329 | 4 | 4 | 8 | 11 |
| Antibody 2 | 316 | 2 | 10 | 11 | 5 |
| Antibody 3 | 290 | 4 | 6 | 10 | 11 |
| Antibody 4 | 273 | 1 | 18 | 13 | 7 |
| Antibody 5 | 331 | 4 | 9 | 1 | 3 |

Example 8

Specificity Testing of Anti-Complex IgG by ELISA

IgG were tested for specific binding to the complex using ELISA as described in the Materials and Methods section.

TABLE 4

Specificity ELISA data of IgG to IL-6/sIL-6R complex when incubated with 50 nM of protein

| | Europium Counts | | | | | |
|---|---|---|---|---|---|---|
| Clone | Ligand | Receptor | Complex 1 | Complex 2 | HYPER | Irrelevant |
| Antibody 1 | 2620 | 1344 | 18722 | 68049 | 161823 | 1364 |
| Antibody 2 | 2647 | 2448 | 154957 | 450867 | 344773 | 1831 |
| Antibody 3 | 2090 | 1421 | 17297 | 40928 | 96027 | 1745 |
| Antibody 4 | 2054 | 2000 | 97315 | 387428 | 310693 | 1602 |
| Antibody 5 | 1726 | 1504 | 119647 | 417485 | 382951 | 1681 |

Materials and Methods
Key Reagents
- IL-6 was sourced from R&D Systems (206-IL/CF)
- Soluble IL-6 receptor (sIL-6R) was sourced from Peprotech (200-06R)
- HIS FLAG IL-6 was provided by AstraZeneca (*E. coli* derived)
- HIS FLAG sIL-6R was prepared in-house at Cambridge Antibody Technology (HEK-EBNA derived)
- Hyper-IL-6 (covalently linked IL-6 and sIL-R via a linker) was provided by AstraZeneca (HEK-EBNA derived)
- Recombinant gp130-Fc was obtained from R&D systems (671-GP). The gp130-Fc was produced from a DNA sequence encoding the extra cellular domain of the human gp130 sequence (Hibi et al; Cell 63:1149-1157) fused to the carboxy-terminal 6× histidine-tagged Fc region of human IgG1 via a polypeptide linker. The chimeric protein was expressed in a mouse myeloma cell line NS0.

Isolation of Antibodies to the Human IL-6/sIL-6R Complex from Naïve Phage Display Libraries Naïve human single chain Fv (scFv) phage display libraries cloned in to a phagemid vector based on the filamentous phage M13 were used for selections [73, 74]. For each selection, 500 µl of streptavidin coated paramagnetic beads (Dynal M280, 602.10) were captured on a magnet then re-suspended in 500 µl of 50 µg/ml biotinylated anti-FLAG monoclonal antibody (Sigma F9291) in Dulbecco's Phosphate Buffered Saline (PBS) pH 7.4 for 1 h to coat the beads. The beads were washed 3 times PBS containing 0.05% Tween 20 (PBST) then incubated in 500 µl 3% (w/v) skimmed milk powder (Premier Brands) in PBS (MPBS) for 1 h to block any non-specific binding sites.

A 50 µl library aliquot containing approximately $1 \times 10^{12}$ phage particles was diluted to 400 µl and used to re-suspend the anti-FLAG coated beads recovered from 150 µl of the blocked solution. Phage were then incubated with the beads on a rotator for 1 h. In addition, for some of the selection procedures, de-selection against a 10-fold excess of the untagged protein used to form the complex was incorporated in conjunction with the de-selection step against the treated paramagnetic beads. The beads were then removed by capturing on a magnet. A 100 µl volume of a 5 times concentrate complex stock solution (500 nM FLAG-tagged protein and 1 µM untagged protein) was added to the de-selected library and incubated for 2 hrs. Phage bound to the FLAG-tagged complex were captured by incubating with the remaining 350 µl of treated paramagnetic beads for 15 mins on a rotator. The beads were washed 5 times in 0.9 mL PBST to remove unbound phage particles. Bound phage were then eluted from the beads by incubation in 500 µl 10 µg/mL trypsin in 0.1 M sodium phosphate, pH 7.0 for 30 mins at 37° C. Infection of *E. coli* TG-1 cells with the eluted phage and phage rescue for subsequent selection rounds was done essentially as described by Marks et al 1991 [75] using trypsin cleavable helper phage [76].

Hyper IL-6/gp130 Fc Binding HTRF® Assay (Crude Periplasmic Preparations)

Hyper IL-6/gp130 Fc binding HTRF® (Homogeneous Time-Resolved Fluorescence) assay for the inhibition of FLAG HIS tagged Hyper IL-6 (In house HEK-EBNA expressed) binding to recombinant human gp130 Fc (R&D systems 671-GP).

Selection outputs were screened as undiluted crude scFv containing periplasmic extracts prepared in 50 mM MOPS buffer pH 7.4, 0.5 mM EDTA and 0.5 M Sorbitol. 10 µl of crude scFv sample was added to a black 384 well optiplate (Perkin Elmer 6007279) assay plate. This was followed by addition of 4 nM gp130 Fc (10 µl/well), 4 nM Hyper IL-6 (10 µl/well) and combined HTRF reagents 1.732 nM anti-flag IgG labelled with cryptate (CIS Bio International 61FG2KLB) and 20 nM anti-human Fc antibody labelled with XL665 (CIS Bio International 61HFCXLA). All dilutions were performed in PBS containing 0.4 M potassium fluoride and 0.1% BSA (assay buffer). Plates were incubated for 3 h at room temperature, prior to reading time resolved fluorescence at 620 nm and 665 nm emission wavelengths using an EnVision plate reader (Perkin Elmer). Data was analysed by calculating % delta F and % specific binding as described in equation 1 and equation 2.

$$\% \text{ Delta } F = \frac{(\text{sample 665 nM/620 nM ratio value}) - (\text{non-specific control 665 nM/620 nM ratio value})}{(\text{non-specific control 665 nM/620 nM ratio value})} \times 100 \qquad \text{Equation 1}$$

$$\% \text{ specific binding} = \frac{\% \text{ Delta } F \text{ of sample}}{\% \text{ Delta } F \text{ of total binding control}} \times 100 \qquad \text{Equation 2}$$

Hyper IL-6/GP130 Fc Binding HTRF® Assay (Purified scFv Preparations)

HTRF® assay for inhibition of binding of FLAG HIS tagged Hyper IL-6 to recombinant human gp130 Fc.

Purified scFv were diluted 1:3 by transferring 15 µl of purified scFv to 30 µl assay buffer and mixing by pipetting in 96 well plate (Greiner 650201). Dilutions were carried out sequentially in duplicate a further 9 times. 3 nM GP130 Fc (10 µl/well) to give a final concentration of 0.5 nM, 6 nM Hyper IL-6 (10 µl/well) to give a final concentration of 1 nM and combined HTRF reagents 2.598 nM anti-flag IgG labelled with cryptate and 30 nM anti-human Fc antibody labelled with XL665 (10 µl/well) were added to 30 µl of purified scFv titration in 96 well plate. 40 µl was then transferred to a black 384 well optiplate. All dilutions were performed in assay buffer. As a positive control, for inhibition of binding, human IL-6 ligand/soluble IL-6 receptor complex, (500 nM IL-6 and 500 nM sIL-6R) was included in all assays.

Plates were incubated for 3 h at room temperature, prior to reading time resolved fluorescence at 620 nm and 665 nm emission wavelengths using an EnVision plate reader. Data was analysed by calculating % delta F and % specific binding as described in equation 1 and equation 2. $IC_{50}$ values were determined using GraphPad Prism software by curve fitting using a four-parameter logistic equation (Equation 3).

Equation 3:

$$Y = \text{Bottom} + (\text{Top} - \text{Bottom})/(1 + 10^{((\text{LogEC50} - X) \cdot \text{HillSlope})})$$

X is the logarithm of concentration. Y is specific binding Y starts at Bottom and goes to Top with a sigmoid shape.

Phage ELISA Screen to Identify Complex Specific scFv

Production of phage from individual cultures in 400 µl volumes was done essentially as described by Marks et al 1991 [75]. Overnight phage cultures were blocked by addition of 400 µl MPBS and incubated for 1 h. The cultures were spun in a Sorval RT6000D benchtop centrifuge at 3000 rpm for 10 mins. The supernatants were then removed for testing.

A sufficient number of streptavidin coated immunoassay plates (Abgene AB1226) were treated with 50 µl/well of 1 µg/mL biotinylated anti FLAG monoclonal antibody in PBS and incubated overnight (ca.16 hs) at 4° C. The immunoassay plates were then washed 3 times with PBST. All wells were then blocked by addition of 300 μl MPBS and incubated for 1 h. Each plate was washed as previously described, then treated with 50 μl/well of one of the following test reagents; 0.5 μg/ml HIS FLAG IL-6, 1 μg/ml HIS FLAG tagged sIL-6R, 1.5 μg/ml IL-6 complex consisting HIS FLAG IL-6 (0.5 μg/ml) and sIL-6R (1 μg/ml), 1.5 μg/ml IL-6 complex consisting of HIS FLAG sIL-6R (1 μg/ml) and IL-6 (0.5 μg/ml), 1.5 μg/ml Hyper IL-6, or MPBS. Complexes were formed by pre-incubating the reagents together for 10 mins prior to addition to the plates. The plates were then incubated for 1 h. After a further washing step, 50 μl of each blocked culture supernatant was added to each of the differently treated plates and incubated for 1 h. The plates were again washed before 50 μl of horseradish peroxidase conjugated anti M13 (Amersham 27-9421-01) diluted 1 in 5000 in MPBS was added to all wells and incubated for a further h. Following the final wash step, 50 μl of 3,3,5,5,-tetramethylbenzidine (Sigma T0440) was added to all wells and incubated for approximately 3 mins. The reactions in all wells were then stopped by addition of 50 μl 0.5 M $H_2SO_4$, and the optical densities at 450 nm determined using an EnVision plate reader.

Specificity Testing of Anti-Complex IgG Using a HTRF® Soluble Assay

A titration of FLAG HIS Hyper IL-6, FLAG HIS IL-6 and FLAG HIS sIL-6R was used in order to establish whether IgG bound to each of these proteins. Titrations were performed in assay buffer (1:3 dilutions) from 160 nM. An irrelevant FLAG HIS ligand and FLAG HIS receptor were included as controls.

5 μl of each titration was transferred to a 384 well low volume assay plate (Costar 3676). 4 nM of in house IgG was then added (5 μl/well), followed by 3.2 nM of anti-flag IgG labelled with XL665 (CIS Bio 61FG2XLB) and 60 nM anti-human Fc antibody labelled with europium cryptate (CIS Bio 61HFCKLB) (5 μl/well). All dilutions were performed in assay buffer.

Assay plates were then centrifuged at 1000 rpm at room temperature for 1 min, and incubated for 3 h at room temperature, prior to reading time resolved fluorescence at 620 nm and 665 nm emission wavelengths using an EnVision plate reader.

Data was analysed by calculating % Delta F values for each sample as previously described.

Specificity Testing of Anti-Complex IgG by ELISA

For each antibody being tested, a 96-well immunoassay plates (Nunc Maxisorp) were coated with 50 μl/well of 2 μg/ml anti-human Fc monoclonal antibody (Jackson Immunoresearch 109-005-098) in PBS overnight (ca.16h) at 4° C. Immunoassay plates were washed 3 times using PBST, then blocked by addition of 300 μl/well MPBS for 1 h at room temperature. After a second washing step 2 μg/ml of the anti-complex antibody in PBS was added to the plate at 50 μl/well. The plates were incubated for 1 h at room temperature before being washed again as previously described. FLAG-tagged reagents (IL-6, sIL-6R, Hyper Complexes) were diluted to 50 nM in MPBS. Complexes were made using 50 nM of the FLAG-tagged component and a 2-fold molar excess of the untagged component. Four-fold serial dilutions were prepared of each of the reagents, which were then added to duplicate wells of the immunoassay plates at 50 μl/well. Control wells containing 50 nM irrelevant protein (in this case his FLAG tagged murine GMCSF-R), or MPBS only were also prepared. The immunoassay plates were then incubated for 1 h at room temperature. After a further washing step, biotinylated anti-FLAG monoclonal antibody (Sigma) diluted to 1 μg/ml in MPBS was added to all wells at 50 μl/well. The plates were incubated for 1 h at room temperature before the plates were again washed as before. Europium labelled streptavidin (Perkin Elmer 1244-360) was diluted to 100 ng/ml in Delfia assay buffer (Perkin Elmer 4002-0010), added to all wells at 50 μl/well and incubated for 1 h at room temperature. The immunoassay plates were then washed 7 times in Delfia wash buffer, consisting of 0.05 M Tris buffered saline (NaCl-0.138 M, KCl-0.0027 M) Tween 20 (0.05%), pH 8.0 (at 25° C.). A 50 μl volume of Delfia enhancement solution (Perkin Elmer 4001-0010) was then added to all wells. The plates were incubated for 10 mins before the Time-resolved fluorescence was measured at 620 nm using an EnVision plate reader.

SEQUENCES

Sequences of binding members of the invention are shown in the appended sequence listing, in which SEQ ID NOS correspond as follows:

| | |
|---|---|
| 1 | Antibody 1 VH nucleotide |
| 2 | Antibody 1 VH amino acid |
| 3 | Antibody 1 VH CDR 1 aa |
| 4 | Antibody 1 VH CDR 2 aa |
| 5 | Antibody 1 VH CDR 3 aa |
| 6 | Antibody 1 VL nucleotide |
| 7 | Antibody 1 VL amino acid |
| 8 | Antibody 1 VL CDR 1 aa |
| 9 | Antibody 1 VL CDR 2 aa |
| 10 | Antibody 1 VL CDR 3 aa |
| 11 | Antibody 2 VH nucleotide |
| 12 | Ab 2 VH amino acid |
| 13 | Ab 2 VH CDR 1 amino acid |
| 14 | Ab 2 VH CDR 2 amino acid |
| 15 | Ab 2 VH CDR 3 amino acid |
| 16 | Ab 2 VL nucleotide |
| 17 | Ab 2 VL amino acid |
| 18 | Ab 2 VL CDR 1 amino acid |
| 19 | Ab 2 VL CDR 2 amino acid |
| 20 | Ab 2 VL CDR 3 amino acid |
| 21 | Antibody 3 VH nucleotide |
| 22 | Ab 3 VH amino acid |
| 23 | Ab 3 VH CDR 1 amino acid |
| 24 | Ab 3 VH CDR 2 amino acid |
| 25 | Ab 3 VH CDR 3 amino acid |
| 26 | Ab 3 VL nucleotide |
| 27 | Ab 3 VL amino acid |
| 28 | Ab 3 VL CDR 1 amino acid |
| 29 | Ab 3 VL CDR 2 amino acid |
| 30 | Ab 3 VL CDR 3 amino acid |
| 31 | Antibody 4 VH nucleotide |
| 32 | Ab 4 VH amino acid |
| 33 | Ab 4 VH CDR 1 amino acid |
| 34 | Ab 4 VH CDR 2 amino acid |
| 35 | Ab 4 VH CDR 3 amino acid |
| 36 | Ab 4 VL nucleotide |
| 37 | Ab 4 VL amino acid |
| 38 | Ab 4 VL CDR 1 amino acid |
| 39 | Ab 4 VL CDR 2 amino acid |
| 40 | Ab 4 VL CDR 3 amino acid |
| 41 | Antibody 5 VH nucleotide |
| 42 | Ab 5 VH amino acid |
| 43 | Ab 5 VH CDR 1 amino acid |
| 44 | Ab 5 VH CDR 2 amino acid |
| 45 | Ab 5 VH CDR 3 amino acid |
| 46 | Ab 5 VL nucleotide |
| 47 | Ab 5 VL amino acid |
| 48 | Ab 5 VL CDR 1 amino acid |
| 49 | Ab 5 VL CDR 2 amino acid |
| 50 | Ab 5 VL CDR 3 amino acid |
| 51 | Full length human IL-6 amino acid |
| 52 | HIS FLAG tagged human IL-6 |
| 53 | soluble IL-6Ra (human) |
| 54 | FLAG HIS tagged soluble IL-6Ra |
| 55 | Hyper IL-6 |

| | |
|---|---|
| 56 | FLAG HIS tagged Hyper IL-6 |
| 57 | Full length transmembrane IL-6Ra (human) |
| 58 | Human gp130 amino acid |
| 59 | Mature human IL-6 amino acid |

PRT = amino acid sequence

REFERENCES

All references cited anywhere in this specification, including those cited anywhere above, are incorporated herein by reference in their entirety and for all purposes.

1 Haan & Maggos (2004) BioCentury, 12(5): A1-A6
2 Koide et al. (1998) Journal of Molecular Biology, 284: 1141-1151.
3 Nygren et al. (1997) Current Opinion in Structural Biology, 7: 463-469
4 Wess, L. In: BioCentury, The Bernstein Report on BioBusiness, 12(42), A1-A7, 2004
5 Kabat, E. A. et al, Sequences of Proteins of Immunological Interest. 4$^{th}$ Edition. US Department of Health and Human Services. 1987
6 Martin, A. C. R. Accessing the Kabat Antibody Sequence Database by Computer PROTEINS: Structure, Function and Genetics, 25 (1996), 130-133
7 Kabat, E. A. et al. (1991) Sequences of Proteins of Immunological Interest, 5th Edition. US Department of Health and Human Services, Public Service, NIH, Washington
8 Segal et al., PNAS, 71:4298-4302, 1974
9 Amit et al., Science, 233:747-753, 1986
10 Chothia et al., J. Mol. Biol., 196:901-917, 1987
11 Chothia et al., Nature, 342:877-883, 1989
12 Caton et al., J. Immunol., 144:1965-1968, 1990
13 Sharon et al., PNAS, 87:4814-4817, 1990
14 Sharon et al., J. Immunol., 144:4863-4869, 1990
15 Kabat et al., J. Immunol., 147:1709-1719, 1991
16 Holliger & Hudson, Nature Biotechnology 23(9):1126-1136 2005
17 Kontermann, R & Dubel, S, Antibody Engineering, Springer-Verlag New York, LLC; 2001, ISBN: 3540413545
18 Mendez, M. et al. (1997) Nature Genet, 15(2): 146-156
19 Knappik et al. J. Mol. Biol. (2000) 296, 57-86
20 Krebs et al. Journal of Immunological Methods 254 2001 67-84
21 Ward, E. S. et al., Nature 341, 544-546 (1989)
22 McCafferty et al (1990) Nature, 348, 552-554
23 Holt et al (2003) Trends in Biotechnology 21, 484-490
24 Bird et al, Science, 242, 423-426, 1988
25 Huston et al, PNAS USA, 85, 5879-5883, 1988
26 Holliger, P. et al, Proc. Natl. Acad. Sci. USA 90 6444-6448, 1993
27 Reiter, Y. et al, Nature Biotech, 14, 1239-1245, 1996
28 Hu, S. et al, Cancer Res., 56, 3055-3061, 1996
29 Qui et al., Nat. Biotechnol. 25:921-929 2007
30 Holliger and Bohlen 1999 Cancer and metastasis rev. 18: 411-419
31 Holliger, P. and Winter G. Current Opinion Biotechnol 4, 446-449 1993
32 Glennie M J et al., 1987 J. Immunol. 139, 2367-2375
33 Repp R. et al., 1995 J. Hemat. 377-382
34 Staerz U. D. and Bevan M. J. 1986 PNAS 83
35 Suresh M. R. et al., 1986 Method Enzymol. 121: 210-228
36 Merchand et al., 1998 Nature Biotech. 16:677-681
37 Ridgeway, J. B. B. et al, Protein Eng., 9, 616-621, 1996
38 Harlow and Lane, Antibodies: A Laboratory Manual, Cold Spring Harbor Laboratory, Cold Spring Harbor N.Y., pp. 726, 1988
39 Köhler and Milstein, Nature, 256:495-497, 1975
40 Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
41 Norman et al. Applied Regression Analysis. Wiley-Interscience; 3$^{rd}$ edition (April 1998) ISBN: 0471170828
42 Kandel, Abraham & Backer, Eric. Computer-Assisted Reasoning in Cluster Analysis. Prentice Hall PTR, (May 11, 1995), ISBN: 0133418847
43 Krzanowski, Wojtek. Principles of Multivariate Analysis: A User's Perspective (Oxford Statistical Science Series, No 22 (Paper)). Oxford University Press; (December 2000), ISBN: 0198507089
44 Witten, Ian H. & Frank, Eibe. Data Mining: Practical Machine Learning Tools and Techniques with Java Implementations. Morgan Kaufmann; (Oct. 11, 1999), ISBN: 1558605525
45 Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369
46 Ghose, Arup K. & Viswanadhan, Vellarkad N. Combinatorial Library Design and Evaluation Principles, Software, Tools, and Applications in Drug Discovery. ISBN: 0-8247-0487-8
47 Chothia C. et al. Journal Molecular Biology (1992) 227, 799-817
48 Al-Lazikani, et al. Journal Molecular Biology (1997) 273 (4), 927-948
49 Chothia, et al. Science, 223, 755-758 (1986)
50 Whitelegg, N. R. u. and Rees, A. R (2000). Prot. Eng., 12, 815-824
51 Guex, N. and Peitsch, M. C. Electrophoresis (1997) 18, 2714-2723
52 Altschul et al. (1990) J. Mol. Biol. 215: 405-410
53 Pearson and Lipman (1988) PNAS USA 85: 2444-2448
54 Smith and Waterman (1981) J. Mol. Biol. 147: 195-197
55 Voet & Voet, Biochemistry, 2nd Edition, (Wiley) 1995.
56 Gram et al., 1992, Proc. Natl. Acad. Sci., USA, 89:3576-3580
57 Barbas et al., 1994, Proc. Natl. Acad. Sci., USA, 91:3809-3813
58 Schier et al., 1996, J. Mol. Biol. 263:551-567
59 Marks et al Bio/Technology, 1992, 10:779-783
60 Kay, B. K., Winter, J., and McCafferty, J. (1996) Phage Display of Peptides and Proteins: A Laboratory Manual, San Diego: Academic Press
61 Hunter W. M. and Greenwood F. C. (1962) Nature 194:495
62 Plückthun, A. Bio/Technology 9: 545-551 (1991)
63 Chadd H E and Chamow S M (2001) Current Opinion in Biotechnology 12: 188-194
64 Andersen D C and Krummen L (2002) Current Opinion in Biotechnology 13: 117
65 Larrick J W and Thomas D W (2001) Current Opinion in Biotechnology 12:411-418
66 Sambrook and Russell, Molecular Cloning: a Laboratory Manual: 3rd edition, 2001, Cold Spring Harbor Laboratory Press
67 Ausubel et al. eds., Short Protocols in Molecular Biology: A Compendium of Methods from Current Protocols in Molecular Biology, John Wiley & Sons, 4$^{th}$ edition 1999

68 Robinson, J. R. ed., Sustained and Controlled Release Drug Delivery Systems, Marcel Dekker, Inc., New York, 1978
69 Ledermann J. A. et al. (1991) Int. J. Cancer 47: 659-664
70 Bagshawe K. D. et al. (1991) Antibody, Immunoconjugates and Radiopharmaceuticals 4: 915-922
71 Persic, L., et al. (1997) *Gene* 187, 9-18.
72 Mach et al Anal. Biochem. 200(1): 20-26, 1992
73 Vaughan, T. J., et al. (1996). *Nature Biotechnology* 14, 309-314.
74 Hutchings, C. Generation of Naïve Human Antibody Libraries, in Antibody Engineering, R. Kontermann and S. Dubel, Editors. 2001, Springer Laboratory Manuals, Berlin. p. 93
75 Marks, J. D., et al. (1991). *Journal of Molecular Biology* 222, 581-597.
76 Kristensen, P., Winter G. (1998). *Folding and Design* 3 (5), 321-328.

The invention claimed is:

1. An isolated antibody, wherein the antibody binds IL-6:IL-6Ra complex formed by IL-6 and IL-6Ra, and does not bind either IL-6 or IL-6Ra alone, wherein the antibody comprises a set of CDRs: HCDR1, HCDR2, HCDR3, LCDR1, LCDR2 and LCDR3, wherein:
   a) HCDR1 comprises the amino acid sequence of SEQ ID NO: 3, HCDR2 comprises the amino acid sequence of SEQ ID NO: 4, HCDR3 comprises the amino acid sequence of SEQ ID NO: 5, LCDR1 comprises the amino acid of sequence SEQ ID NO: 8, LCDR2 comprises the amino acid sequence of SEQ ID NO: 9, and LCDR3 comprises the amino acid sequence of SEQ ID NO: 10; or
   b) HCDR1 comprises the amino acid sequence of SEQ ID NO: 13, HCDR2 comprises amino the acid sequence of SEQ ID NO: 14, HCDR3 comprises the amino acid sequence of SEQ ID NO: 15, LCDR1 comprises the amino acid of sequence SEQ ID NO: 18, LCDR2 comprises the amino acid sequence of SEQ ID NO: 19, and LCDR3 comprises the amino acid sequence of SEQ ID NO: 20; or
   c) HCDR1 comprises the amino acid sequence of SEQ ID NO: 23, HCDR2 comprises amino the acid sequence of SEQ ID NO: 24, HCDR3 comprises the amino acid sequence of SEQ ID NO: 25, LCDR1 comprises the amino acid of sequence SEQ ID NO: 28, LCDR2 comprises the amino acid sequence of SEQ ID NO: 29, and LCDR3 comprises the amino acid sequence of SEQ ID NO: 30.

2. The antibody of claim 1, wherein the antibody inhibits binding of IL-6:IL-6Ra complex to gp130.

3. The antibody of claim 2, wherein the antibody has an IC50 of not more than 700 nM, not more than 30 nM, not more than 25 nM, not more than 1.5 nM or not more than 0.8 nM in a homogenous time-resolved fluorescence assay for inhibition of binding of IL-6:IL-6Ra complex to gp130, with a final concentration of 1 nM complex and 1 nM gp130.

4. The antibody of claim 1, wherein the antibody comprises a VH domain and a VL domain, wherein
   a) the VH domain comprises the amino acid sequence of SEQ ID NO: 2 and the VL domain comprises the amino acid sequence of SEQ ID NO:7; or b) the VH domain comprises the amino acid sequence of SEQ ID NO: 12 and the VL domain comprises the amino acid sequence of SEQ ID NO:17; or
c) the VH domain comprises the amino acid sequence of SEQ ID NO: 22 and the VL domain comprises the amino acid sequence of SEQ ID NO:27.

5. A composition comprising the antibody of claim 1 and a pharmaceutically acceptable excipient.

6. A composition comprising the antibody of claim 4 and a pharmaceutically acceptable excipient.

* * * * *